(12) United States Patent
Uhrich et al.

(10) Patent No.: US 7,262,221 B2
(45) Date of Patent: Aug. 28, 2007

(54) AMPHIPHILIC STAR-LIKE MACROMOLECULES FOR DRUG DELIVERY

(75) Inventors: Kathryn E. Uhrich, Plainfield, NJ (US); Lu Tian, Morrisville, PA (US)

(73) Assignee: Rutgers The State University of New Jersey, New Brunswick, NJ (US)

( * ) Notice: Subject to any disclaimer, the term of this patent is extended or adjusted under 35 U.S.C. 154(b) by 419 days.

(21) Appl. No.: 10/754,900

(22) Filed: Jan. 9, 2004

(65) Prior Publication Data
US 2004/0198641 A1 Oct. 7, 2004

Related U.S. Application Data

(63) Continuation of application No. PCT/US02/21923, filed on Jul. 12, 2002.

(60) Provisional application No. 60/333,310, filed on Nov. 23, 2001, provisional application No. 60/304,965, filed on Jul. 12, 2001.

(51) Int. Cl.
*A61K 31/175* (2006.01)
*C07D 235/02* (2006.01)
*C07C 229/00* (2006.01)
(52) U.S. Cl. .................... 514/587; 548/304.1; 560/171
(58) Field of Classification Search ............. 548/304.1
See application file for complete search history.

(56) References Cited

U.S. PATENT DOCUMENTS

| 4,573,966 A | 3/1986 | Weikl et al. ............... 604/53 |
| 4,597,961 A | 7/1986 | Etscorn ...................... 424/28 |
| 5,126,144 A | 6/1992 | Jaeger et al. |
| 5,132,115 A | 7/1992 | Wolter et al. |
| 5,830,986 A | 11/1998 | Merrill ...................... 528/425 |
| 6,007,845 A | 12/1999 | Domb et al. ............... 424/501 |
| 6,284,233 B1 | 9/2001 | Simon et al. ............ 424/78.03 |

OTHER PUBLICATIONS

Felix, Arthur M., "Site-Specific Poly(ethylene glycol)ylation of Peptides", In: *Poly(ethylene glycol) Chemistry and Biological Applications, ACS Symposium Series 680*, J.M. Harris, et al. (Eds.),(Apr. 1997),99-115/218-225.

Harris, J. M., et al., "ACS Symposium Series", (Apr. 1997),99-115/218-225.

Jiang, S. A., et al., "Tailored Polymeric Materials for Controlled Delivery Systems", *ACS Symposium Series, 709*, American Chemical Society, Washington, DC,(1998),117-124.

Liu, Hongbo , et al., "Hyperbranched polymeric micelles: drug encapsulation, release and polymer degradation", Department of Chemistry, Rutgers University, Piscataway, NJ,pp. 582-583.

*Primary Examiner*—Paul A. Zucker
(74) *Attorney, Agent, or Firm*—Viksnins Harris & Padys LLP

(57) ABSTRACT

The present invention provides polymeric compounds that can form micelles in solutions. These compounds have a hydrophobic, core that is coupled to a plurality of hydrophilic moieties.

58 Claims, 11 Drawing Sheets

Folic Acid

Biotin

AMPHIPHILIC STAR-LIKE MACROMOLECULES FOR DRUG DELIVERY

PRIORITY OF INVENTION

This application is a continuation under 35 U.S.C. § 111(a) of PCT/US02//21923, filed on Jul. 12, 2002 and published in English on Jan. 23, 2003 as WO 03/005959 A2, which claims the benefit of the filing date of U.S. application Ser. No. 60/304,965, filed Jul. 12, 2001 and U.S. application Ser. No. 60/333,310, filed Nov. 23, 2001, under 35 U.S.C. § 119(e), the disclosures of which are incorporated by reference herein in their entirety.

GOVERNMENT FUNDING

The invention described herein was made with government support under Grant Number 99-83272, awarded by the National Science Foundation. The United States Government has certain rights in the invention.

BACKGROUND OF THE INVENTION

Currently, there is a need for methods for delivering pharmaceutically active agents to patients in need of the active agent. One method for delivery is to encapsulate an active agent, such as, for example, a hydrophobic molecule in a polymer molecule wherein the polymer has a core that is coupled to a plurality of hydrophobic moieties.

Amphiphilic star-like macromolecules (ASMs) have been studied for drug delivery applications. (See, e.g., U.S. patent application Ser. No. 09/298,729 filed Apr. 23, 1999; U.S. patent application Ser. No. 09/422,295, filed Oct. 21, 1999, and International Patent Application US00/10050 filed Apr. 18, 2000.) The core-shell, amphiphilic structure of ASMs is covalently linked, which makes it thermodynamically stable as opposed to conventional micellar systems. Previously, aromatic cores were incorporated within the ASM structure but proved to be cytotoxic upon its degradation.

Polymeric micelles are a related type of amphiphilic block copolymers. These micelles have attracted attention as promising colloidal drug delivery systems (V. P. Torchilin J. Controlled. Release. 2001, 73, 137; C. Allen, D. et al., Colloids and Surfaces B: Biointerfaces 1999, 16, 3; and H. Otsuka, et al., Current Opinion in Colloid & Interface Science 2001, 6, 3). In these colloidal systems, the hydrophobic block typically forms the core, essentially a "microcontainer" for a lipophilic pharmaceutical (K. Kataoka, et al., Adv. Drug Delivery Rev. 2001, 47, 113). The hydrophilic part forms the outer shell, stabilizing the interface between the core and the external aqueous environment. Compared to traditional micellar systems, these polymeric surfactant-based drug carriers display apparent advantages such as lower critical micelle concentration (CMC), improved bioavailability, reduction of toxicity, enhanced permeability across the physiological barriers, and substantial changes in drug biodistribution.

Despite these advantages, the use of ASM's is somewhat limited, due to the difficulty in directing the release of the active agent at or near an appropriate target. Accordingly, there is a need for additional micellar systems and reverse micellar systems that possess some of the advantages associated with the thermodynamic stability of ASM's, but which can be used to direct active agents to specific targets.

SUMMARY OF THE INVENTION

The present invention provides a compound having formula (I):

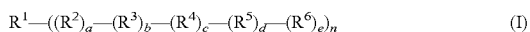

(I)

wherein:

a) $R^1$ is a core comprising a polyol or polyacid;

each $R^2$ independently is a divalent or polyvalent group having the formula $-X^1-R^8-(X^{1a})_g-$, wherein $X^1$ and $X^{1a}$ are independently $-C(=O)-$, $-C(=S)-$, $-O-$, $-S-$, $-N(R^7)-$ or absent, and each $R^8$ is independently $-(C_{1-8})$alkylene-, branched $-(C_{1-8})$alkylene- or $-(C_{6-10})$aryl-; a is 0 or an integer from 1 to about 10; and g is an integer from 1 to about 6;

each $R^3$ independently is a divalent dicarboxylic acid moiety having the formula $-C(=O)-R^9-C(=O)-$, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula $-X^2-R^{10}-(X^{2a})_h-$, wherein $X^2$ is $-C(=O)-$, $-C(=S)-$, $-O-$, $-S-$, $-N(R^7)-$ or absent; $X^{2a}$ is $-C(=O)-$, $-C(=S)-$, $-O-$, $-S-$, or $-N(R^7)-$ and $R^{10}$ is $-(C_{1-8})$alkylene-, branched $-(C_{1-8})$alkylene- or $-(C_{6-10})$aryl-; and c is 0 or an integer from 1 to about 10; and h is an integer from 1 to 6;

each $R^5$ independently is a group having the formula:

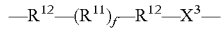

wherein $R^{11}$ is a sugar moiety; or a poly(alkylene oxide) or poly(alkylene imine) group having the formula $-(-X^4-R^{13})-$; wherein $R^{13}$ is $-(C_{2-40})$alkylene- or branched $-(C3_{-40})$alkylene-; wherein each $X^3$ is independently $-C(=O)-$, $-C(=S)-$, $-O-$, $-S-$, $-N(R^7)-$ or absent; each $X^4$ is independently $-O-$, or $-N(R^7)-$; and f is an integer from about 2 to about 150; and d is from 1 to about 6;

each $R^{12}$ is independently a bond, $-(C_{1-40})$alkylene- or branched $-(C_{1-40})$alkylene-groups, wherein each $R^{12}$ is optionally substituted with one or more (e.g., 1, 2, or 3) functional groups. The functional groups are $-OH$, $-OR^a$, $-NR^aR^b$, $-CO_2H$, $-SO_3H$ (sulfo), $-CH_2-OH$, $-CH_2-OR^a$, $-CH_2-O-CH_2-R^a$, and $-CH_2-NR^aR^b$; and $X^4$ is $-O-$, $-S-$, or $-N(R^7)-$;

wherein n is from 2 to 12; provided that a and b are not both zero; wherein each $R^7$ is independently selected from the group consisting of hydrogen, and $C_{(1-40)}$alkyl group, where the alkyl group can be a straight-chain or branched group; and $R^a$ and $R^b$ are each independently hydrogen ($C_{1-8}$)alkyl, aryl, aryl($C_{1-8}$)alkylene; and $R^6$ is hydrogen, are $-OH$, $-OR^a$, $-NR^aR^b$, $-CO_2H$, $-SO_3H$ (sulfo), $-CH_2-OH$, $-CH_2OR^a$, $-CH_2-O-CH_2-R^a$, $-CH_2-R^aR^b$ or a targeting moiety; provided that at least one $R^6$ group is a targeting moiety; and e is from 1 to about 6:

b) $R^1$ is a core comprising a polyol or polyacid;

each $R^2$ independently is a divalent or polyvalent group having the formula $-X^1R^8(X^{1a})_g-$, wherein $X^1$ and $X^{1a}$ are independently $-C(=O)-$, $-C(=S)-$, $-O-$, $-S-$, $-N(R^7)-$ or absent, and each $R^8$ is independently $-(C_{1-8})$alkylene-, branched $-(C_{1-8})$alkylene- or $-(C_{6-10})$aryl-; a is an integer from 1 to about 10; and g is an integer from 1 to about 6;

each $R^3$ independently is a divalent dicarboxylic acid moiety having the formula —C(=O)—$R^9$—C(=O)—, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula —$X^2$—$R^{10}$—($X^{2a}$)$_h$—, wherein $X^2$ is —C(=O)—, —C(=S)—, —O—, —S—, —N($R^7$)— or absent; $X^{2a}$ is —C(=O)—, —C(=S)—, —O—, —S—, or —N($R^7$)— and $R^{10}$ is —($C_{1-8}$)alkylene-, branched —($C_{1-8}$)alkylene- or —($C_{6-10}$)aryl-; and c is 0 or an integer from 1 to about 10; and h is an integer from 1 to 6;

each $R^5$ independently is a group having the formula:

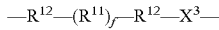

wherein $R^{11}$ is a sugar moiety; or a poly(alkylene oxide) or poly(alkylene imine) group having the formula —(—$X^4$—$R^{13}$)—; wherein $R^{13}$ is —($C_{2-40}$)alkylene- or branched —($C_{3-40}$)alkylene-; wherein each $X^3$ is independently —C(=O)—, —C(=S)—, —O—, —S—, —N($R^7$)— or absent; each $X^4$ is independently —O—, or —N($R^7$)—; and f is an integer from about 2 to about 150; and d is from 1 to about 6;

each $R^{12}$ is independently a bond, —($C_{1-40}$)alkylene- or branched —($C_{1-40}$)alkylene-groups, wherein each $R^{12}$ is optionally substituted with one or more (e.g., 1, 2, or 3) functional groups. The functional groups are —OH, —OR$^a$, —NR$^a$R$^b$, —CO$_2$H, —SO$_3$H (sulfo), —CH$_2$—OH, —CH$_2$OR$^a$, —CH$_2$—O—CH$_2$—R$^a$, and CH$_2$—NR$^a$R$^b$; and $X^4$ is —O—, —S—, or —N($R^7$)—;

wherein n is from 2 to 12; provided that a and b are not both zero; wherein each $R^7$ is independently selected from the group consisting of hydrogen, and $C_{(1-40)}$alkyl group, where the alkyl group can be a straight-chain or branched group; and R$^a$ and R$^b$ are each independently hydrogen ($C_{1-8}$)alkyl, aryl, aryl($C_{1-8}$)alkylene; and $R^6$ is hydrogen, are —OH, —OR$^a$, —NR$^a$R$^b$, —CO$_2$H, —SO$_3$H (sulfo), —CH$_2$—OH, —CH$_2$—OR$^a$, —CH$_2$—O—CH$_2$—R$^a$, —CH$_2$—NR$^a$R$^b$ or a targeting moiety; and e is from 1 to about 6:

c) $R^1$ is a core comprising a polyol or polyacid;

each $R^2$ independently is a divalent or polyvalent group having the formula —$X^1$—$R^8$—($X^{1a}$)$_g$—, wherein $X^1$ and $X^{1a}$ are independently —C(=O)—, —C(=S)—, —O—, —S—, —N($R^7$)— or absent, and each $R^8$ is independently —($C_{1-8}$)alkylene-, branched —($C_{1-8}$)alkylene- or —($C_{6-10}$)aryl-; a is 0 or an integer from 1 to about 10; and g is an integer from 1 to about 6;

each $R^3$ independently is a divalent dicarboxylic acid moiety having the formula —C(=O)—$R^9$—C(=O)—, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula —$X^2$—$R^{10}$—($X^{2a}$)$_h$—, wherein $X^2$ is —C(=O)—, —C(=S)—, —O—, —S—, —N($R^7$)— or absent; $X^{2a}$ is —C(=O)—, —C(=S)—, —O—, —S—, or —N($R^7$)— and $R^{10}$ is —($C_{1-8}$)alkylene-, branched —($C_{1-8}$)alkylene- or —($C_{6-10}$)aryl-; and c is an integer from 1 to about 10; and h is an integer from 1 to 6;

each $R^5$ independently is a group having the formula:

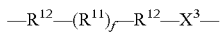

wherein $R^{11}$ is a sugar moiety; or a poly(alkylene oxide) or poly(alkylene imine) group having the formula —(—$X^4$—$R^{13}$)—; wherein $R^{13}$ is —($C_{2-40}$)alkylene- or branched —($C_{3-40}$)alkylene-; wherein each $X^3$ is independently —C(=O)—, —C(=S)—, —O—, —S—, —N($R^7$)— or absent; each $X^4$ is independently —O—, or —N($R^7$)—; and f is an integer from about 2 to about 150; and d is from 1 to about 6;

each $R^{12}$ is independently a bond, —($C_{1-40}$)alkylene- or branched —($C_{1-40}$)alkylene-groups, wherein each $R^{12}$ is optionally substituted with one or more (e.g., 1, 2, or 3) functional groups. The functional groups are —OH, —OR$^a$, —NR$^a$R$^b$, —CO$_2$H, —SO$_3$H (sulfo), —CH$_2$—OH, —CH$_2$—OR$^a$, —CH$_2$—O—CH$_2$—R$^a$, and —CH$_2$—NR$^a$R$^b$; and $X^4$ is —O—, —S—, or —N($R^7$)—;

wherein n is from 2 to 12; provided that a and b are not both zero; wherein each $R^7$ is independently selected from the group consisting of hydrogen, and $C_{(1-40)}$alkyl group, where the alkyl group can be a straight-chain or branched group; and R$^a$ and R$^b$ are each independently hydrogen ($C_{1-8}$)alkyl, aryl, aryl($C_{1-8}$)alkylene; and $R^6$ is hydrogen, are —OH, —OR$^a$, —NR$^a$R$^b$, —CO$_2$H, —SO$_3$H (sulfo), —CH$_2$—OH, —CH$_2$—OR$^a$, —CH$_2$—O—CH$_2$—R$^a$, —CH$_2$—NR$^a$R$^b$ or a targeting moiety; and e is from 1 to about 6:

d) $R^1$ is a core comprising a polyacid moiety having the formula

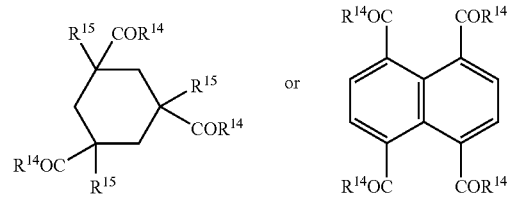

or a pentaerythritol polyol having the formula

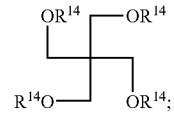

wherein each $R^2$ independently is a divalent or polyvalent group having the formula —$X^1$—$R^8$—($X^{1a}$)$_g$—, wherein $X^1$ and $X^{1a}$ are independently —C(=O)—, —C(=S)—, —O—, —S—, —N($R^7$)— or absent, and each $R^8$ is independently —($C_{1-8}$)alkylene-, branched —($C_{1-8}$)alkylene- or —($C_{6-10}$)aryl-; a is 0 or an integer from 1 to about 10; and g is an integer from 1 to about 6;

each $R^3$ independently is a divalent dicarboxylic acid moiety having the formula —C(=O)—$R^9$—C(=O)—, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula —$X^2$—$R^{10}$—($X^{2a}$)$_h$—, wherein $X^2$ is —C(=O)—, —C(=S)—, —O—, —S—, —N($R^7$)— or absent; $X^{2a}$ is —C(=O)—, —C(=S)—, —O—, —S—, or —N($R^7$)— and $R^{10}$ is —($C_{1-8}$)alkylene-, branched —($C_{1-8}$)

alkylene- or —(C$_{6-10}$)aryl-; and c is 0 or an integer from 1 to about 10; and h is an integer from 1 to 6;

each R$^5$ independently is a group having the formula:

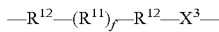

wherein R$^{11}$ is a sugar moiety; or a poly(alkylene oxide) or poly(alkylene imine) group having the formula —(—X$^4$—R$^3$)—; wherein R$^{13}$ is —(C$_{2-40}$)alkylene- or branched —(C$_{3-40}$)alkylene-; wherein each X$^3$ is independently —C(=O)—, —C(=S)—, —O—, —S—, —N(R$^7$)— or absent; each X$^4$ is independently —O—, or —N(R$^7$)—; and f is an integer from about 2 to about 150; and d is from 1 to about 6;

each R$^{12}$ is independently a bond, —(C$_{1-40}$)alkylene- or branched —(C$_{1-40}$)alkylene-groups, wherein each R$^{12}$ is optionally substituted with one or more (e.g., 1, 2, or 3) functional groups. The functional groups are —OH, —OR$^a$, —NR$^a$R$^b$, —CO$_2$H, —SO$_3$H (sulfo), —CH$_2$—OH, —CH$_2$—OR$^a$, —CH$_2$—O—CH$_2$—R$^a$, and —CH$_2$—NR$^a$R$^b$; and X$^4$ is —O—, —S—, or —N(R$^7$)—;

wherein n is from 2 to 12; provided that a and b are not both zero; wherein each R$^7$ is independently selected from the group consisting of hydrogen, and C$_{(1-40)}$alkyl group, where the alkyl group can be a straight-chain or branched group; and R$^a$ and R$^b$ are each independently hydrogen (C$_{1-8}$)alkyl, aryl, aryl(C$_{1-8}$)alkylene; and R$^6$ is hydrogen, are —OH, —OR$^a$, —NR$^a$R$^b$, —NH$_2$, —CO$_2$H, —SO$_3$H (sulfo), —CH$_2$—OH, —CH$_2$—OR$^a$, —CH$_2$—O—CH$_2$—R$^a$, —CH$_2$—NR$^a$R$^b$ or a targeting moiety; and e is from 1 to about 6.

Additionally, compounds of formula (I) having unsaturated bonds (e.g., in the fatty acid or polyether groups), can be cross-linked to form covalently bonds in the hydrophobic portion.

Accordingly, the invention provides a compound of formula (I) as described above. Such compounds of formula (I) are useful intermediates for preparing micelles that can be used in drug delivery applications and that can be cross-linked to provide cross-linked macromolecules that are also useful in drug delivery applications.

The invention also provides an encapsulate comprising a molecule surrounded or partially surrounded by a macromolecule of the invention.

The invention also provides a method for preparing an encapsulate of the invention comprising combining compounds of fonrula (I) and a molecule (e.g., a therapeutic agent) in a solvent, and allowing the compounds of formula (I) to aggregate around the molecule, to provide the encapsulate (i.e., the molecule surrounded or partially surrounded by compounds of formula (I)).

The invention also provides a pharmaceutical composition comprising an encapsulate of the invention (i.e., a therapeutic agent surrounded or partially surrounded by compounds of formula (I)); and a pharmaceutically acceptable carrier.

The invention also provides a pharmaceutical composition comprising an encapsulate of the invention (i.e., a therapeutic agent encapsulated in a cross-linked macromolecule); and a pharmaceutically acceptable carrier.

The invention also provides a method for modulating the release of a therapeutic agent from a pharmaceutical composition comprising administering an encapsulate of the invention to an animal in need of treatment. The encapsulate can modulate the release of therapeutic agents by controlling the adsorption of the active agent encapsulated within the encapsulate through the skin of the animal.

The invention also provides a method for delivering a therapeutic agent to an animal in need of treatment with the agent comprising administering an encapsulate of the invention comprising the agent to the animal.

The invention also provides intermediates and processes useful for preparing compounds of formula (I) as described herein.

The invention also provides for the use of a compound of formula (I) to prepare a medicament useful for treating or preventing an illness or a disease.

The invention also provides a method for using a compound of formula (I) to (a) sequester lipoproteins from macromolecular depots such as proteoglycans that heighten atherogenic tendencies; (b) reduce lipoprotein oxidation (which leads to unregulated uptake of low-density lipoproteins (LDL) by macrophages, transforming them into foam cells, the precursors to atherosclerosis); and (c) enhance lipoprotein transport and clearance (via macrophages, and the liver). The compounds having formula (I) can be administered to a patient in need of reducing the concentration of lipoproteins and minimize cardiovascular diseases caused by the presence of excess LDL in the blood.

DETAILED DESCRIPTION

Figure 1:
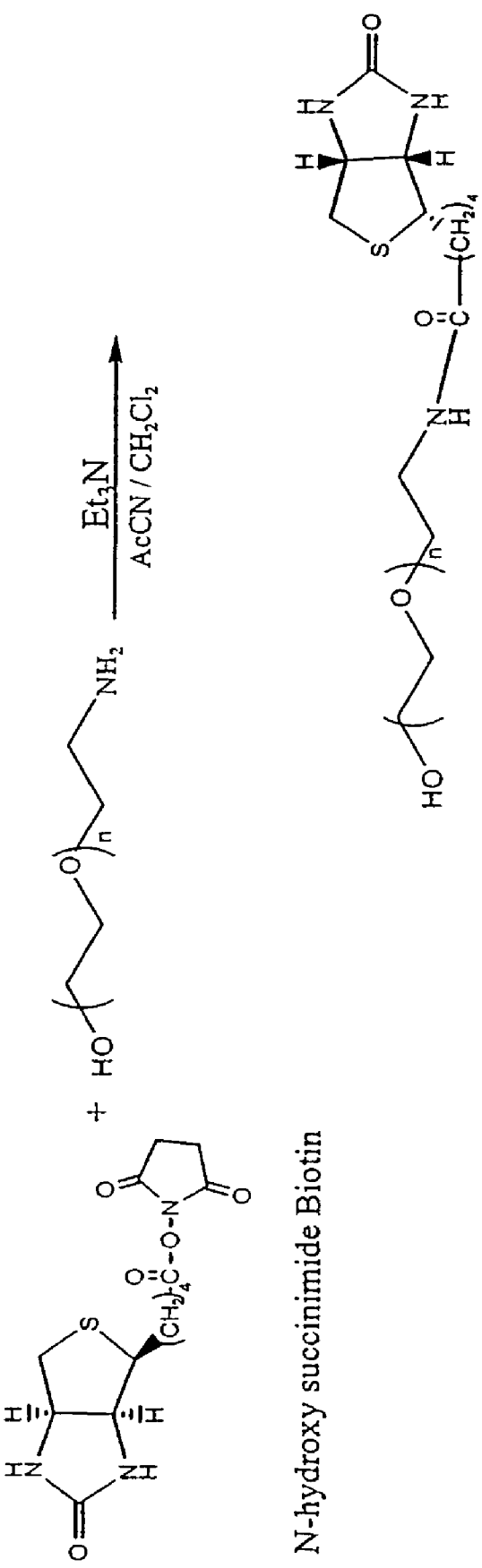
FIGS. 1 and 2 illustrate representative reactions for attaching the targeting moiety, biotin, to a polyalkylene oxide (R$^5$) group.
Figure 2:
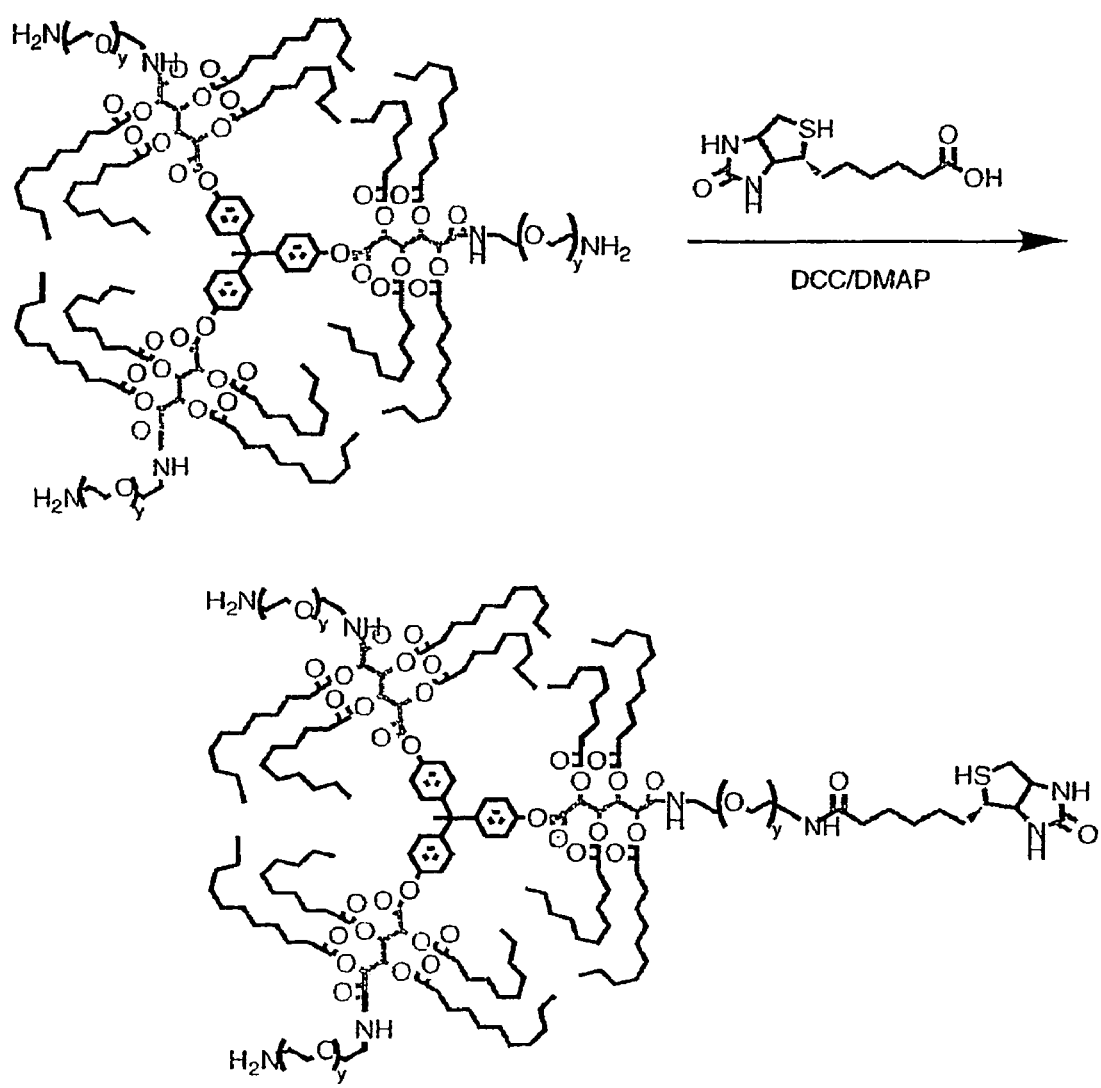
Figure 3:
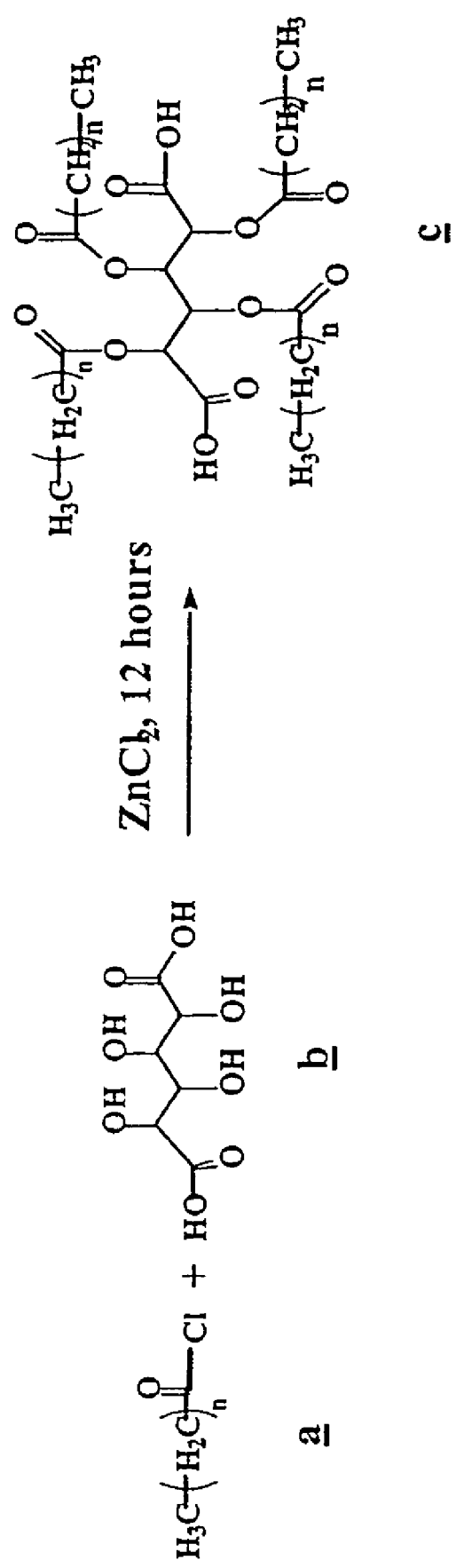
FIG. 3 illustrates a representative reaction for acylation of a divalent dicarboxylic acid moiety, (R$^3$ group).
Figure 4:
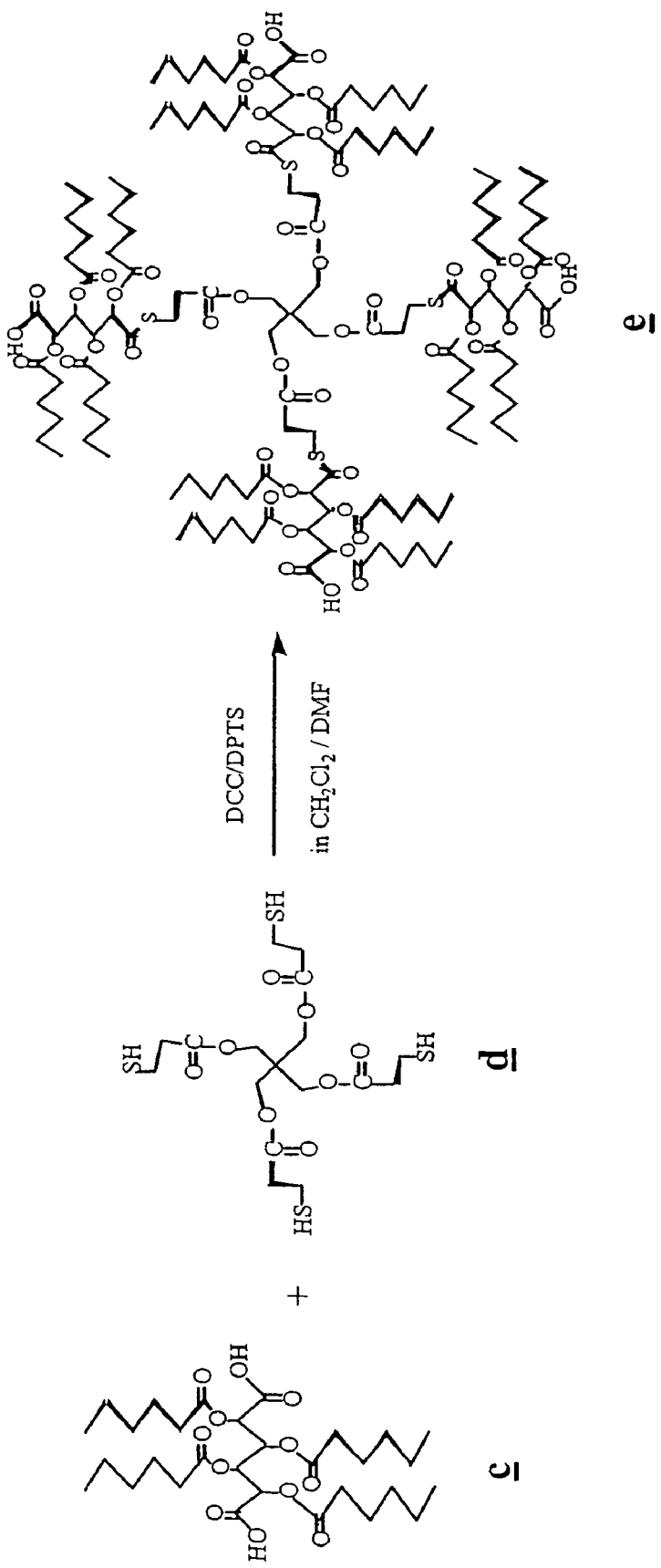
FIG. 4 illustrates a representative reaction for attaching R$^3$ groups to prepare a compound of the invention.
Figure 5:
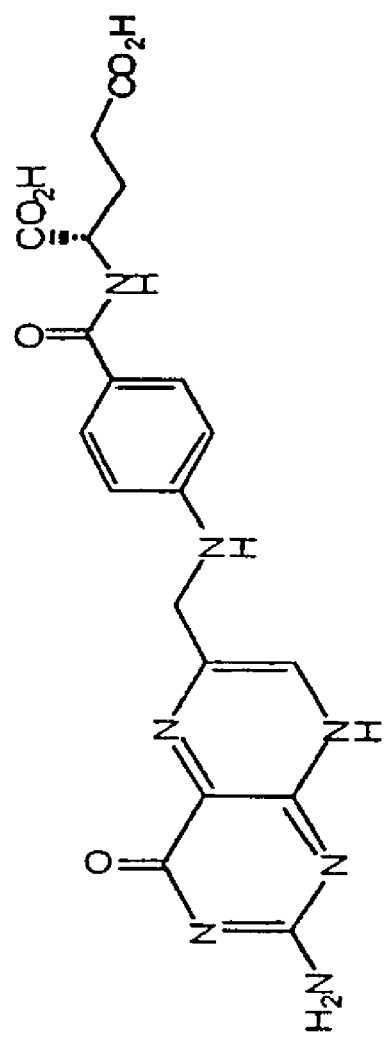
FIG. 5 illustrates two compounds that can be incorporated in the compounds of the invention as targeting moieties.
Figure 5:
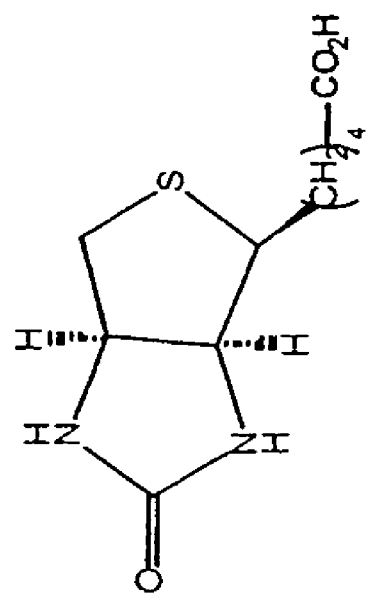
Figure 6:
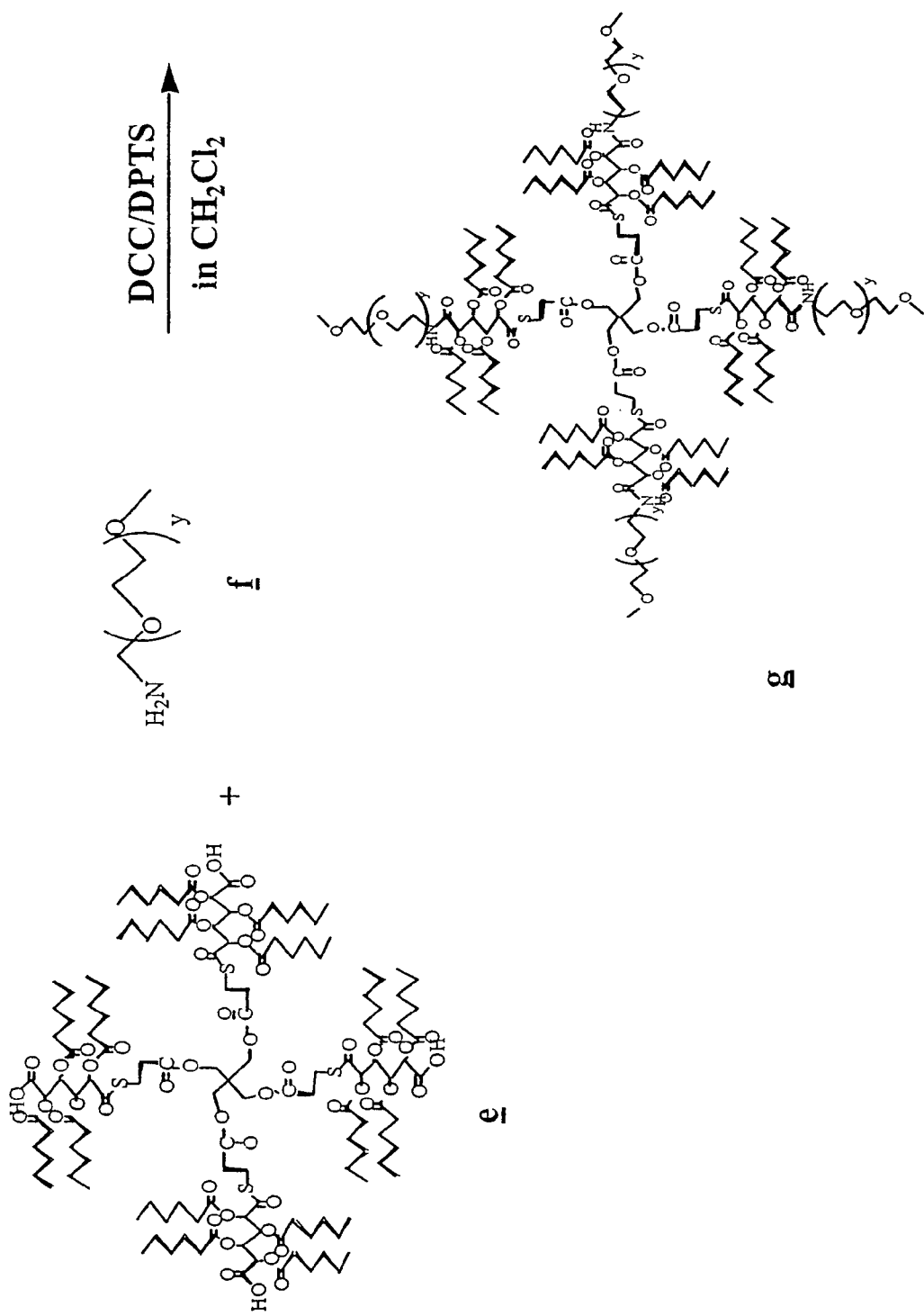
FIG. 6 illustrates a representative reaction for attaching a polyethylene oxide (R$^5$) group to prepare a compound of the invention.
Figure 7:
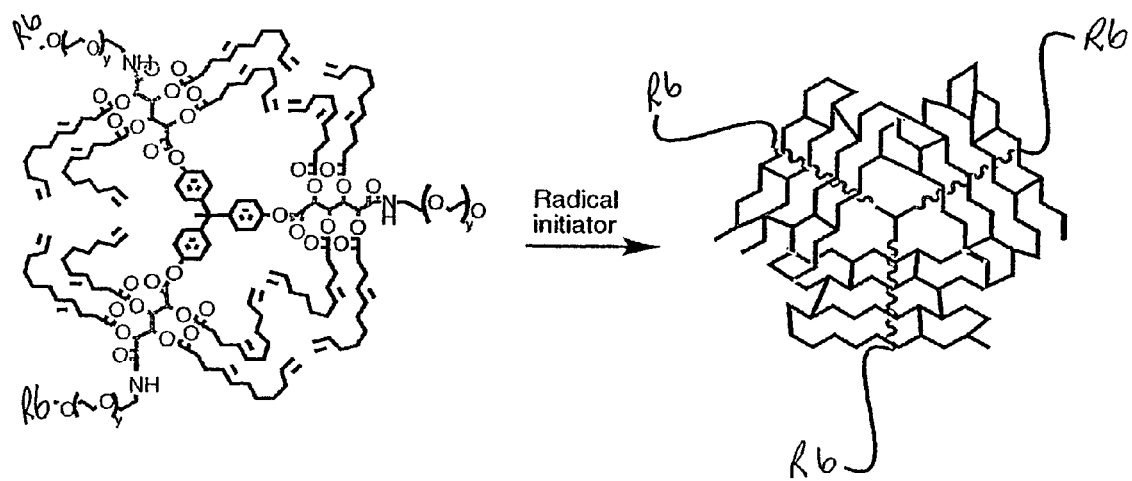
FIG. 7 illustrates a representative reaction for cross-linking the compounds of the invention having unsaturation in the R$^5$ groups to prepare a covalently stabilized compound of the invention.
Figure 8:
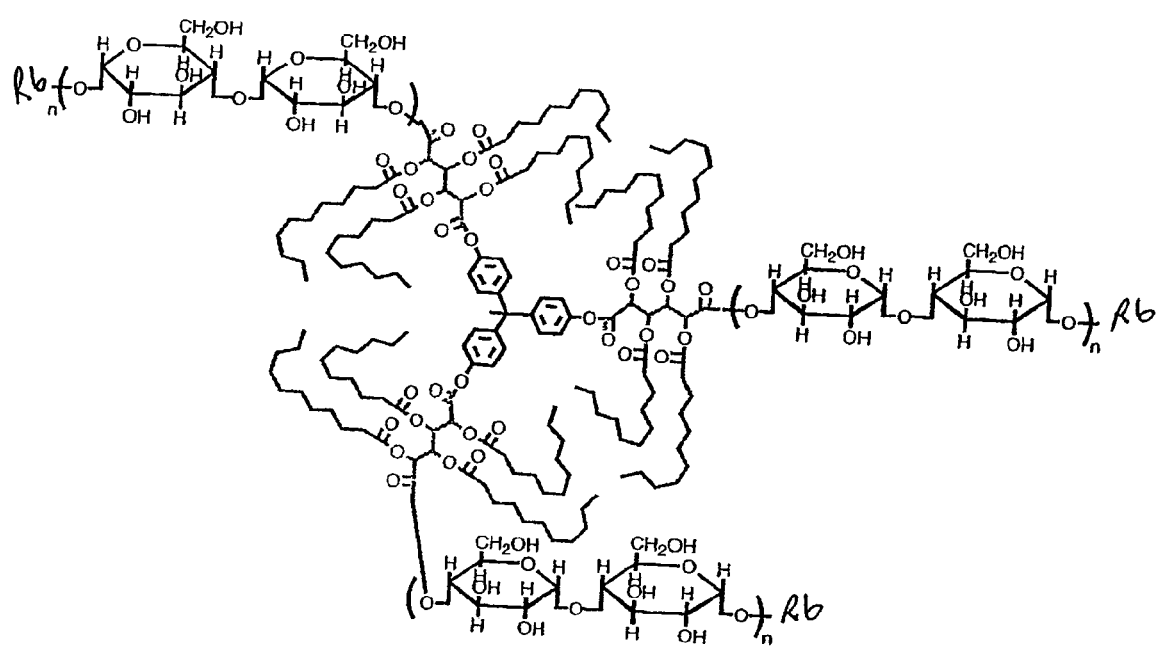
FIGS. 8, 9, 10, and 11 illustrate representative compounds of the invention.
Figure 9:
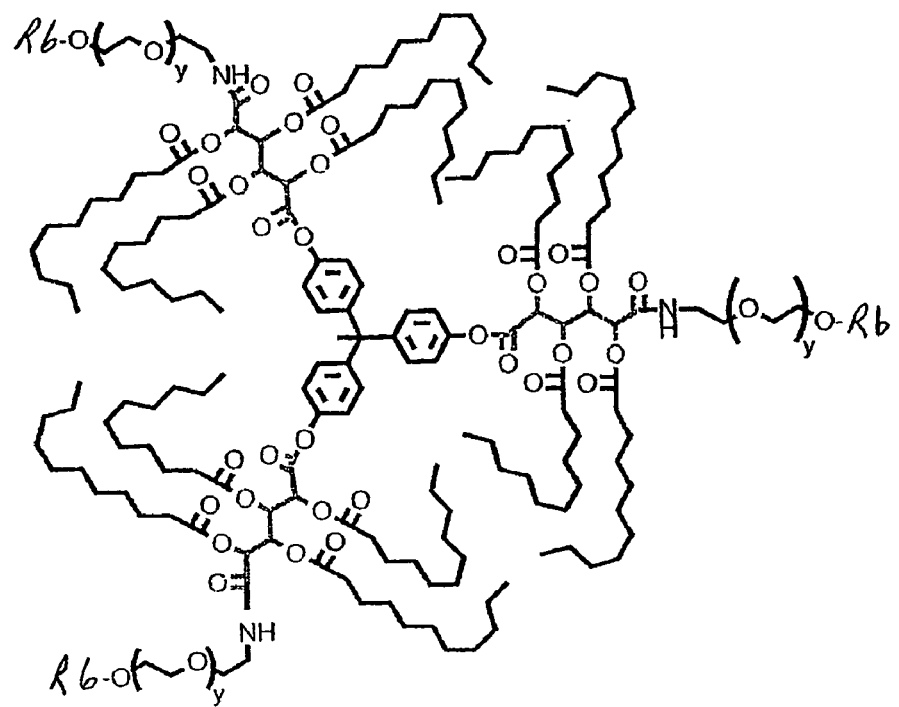
Figure 9:
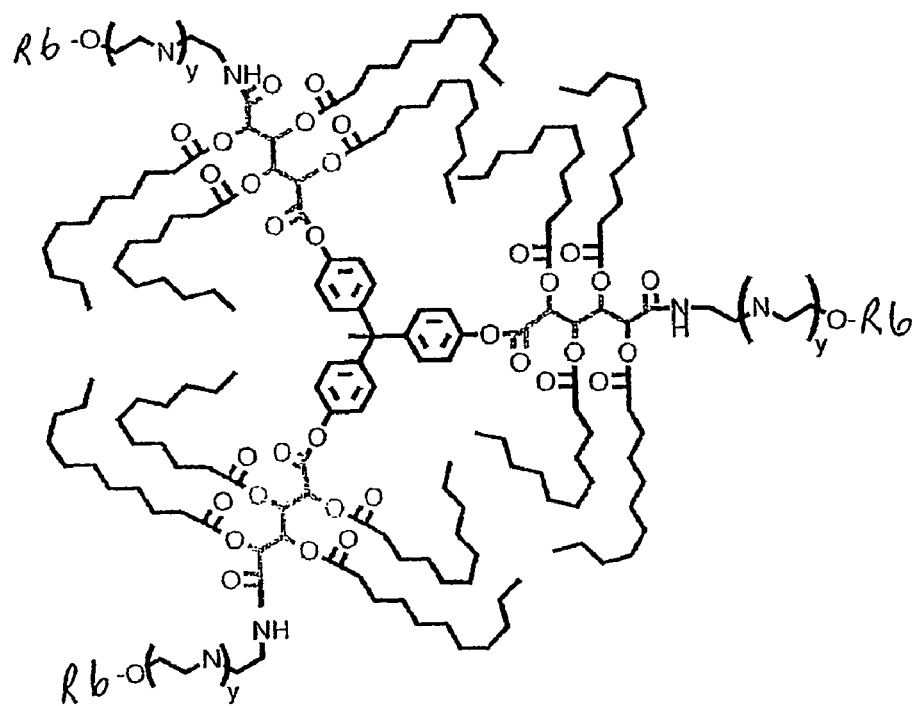
Figure 10:
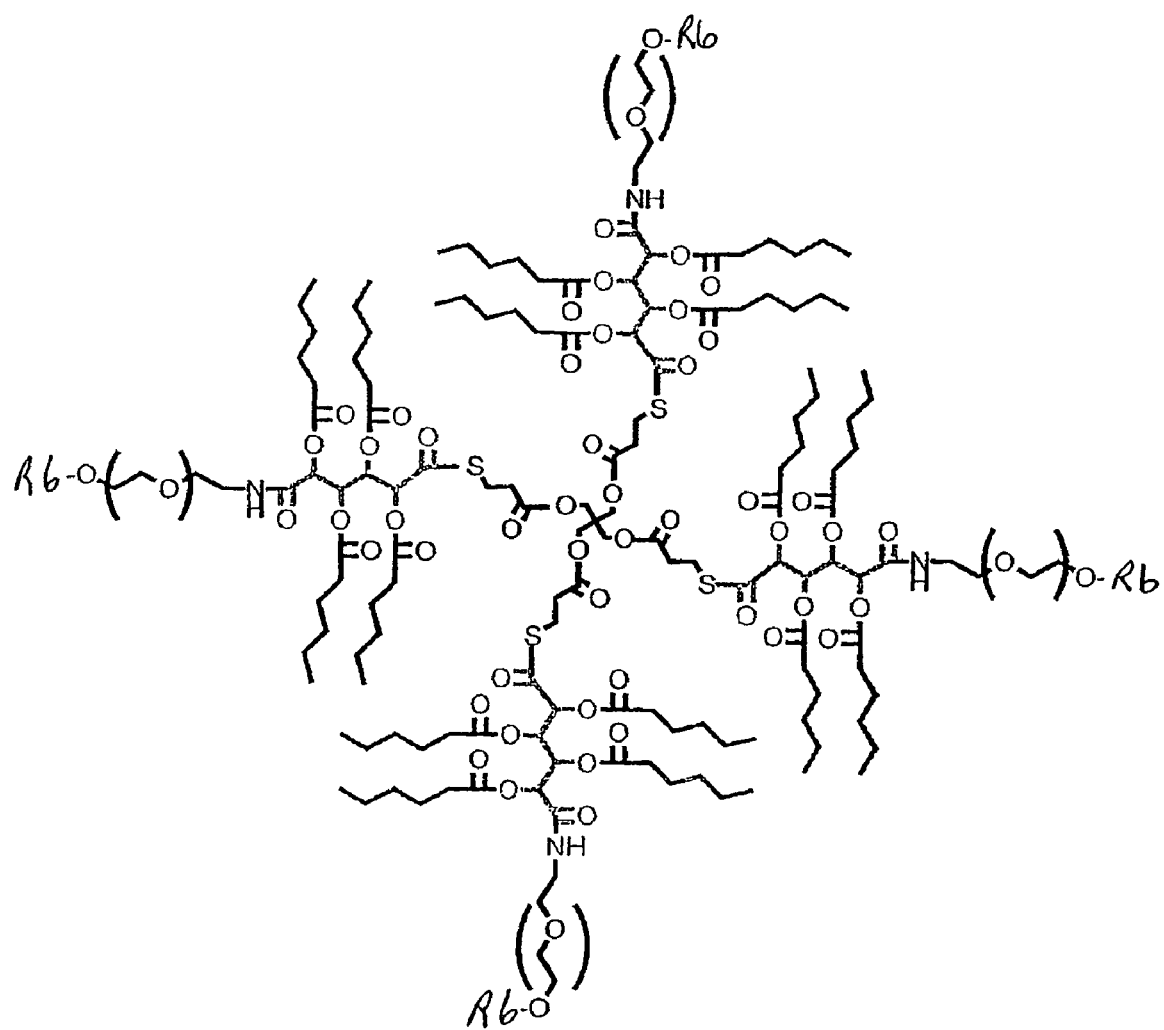
Figure 11:
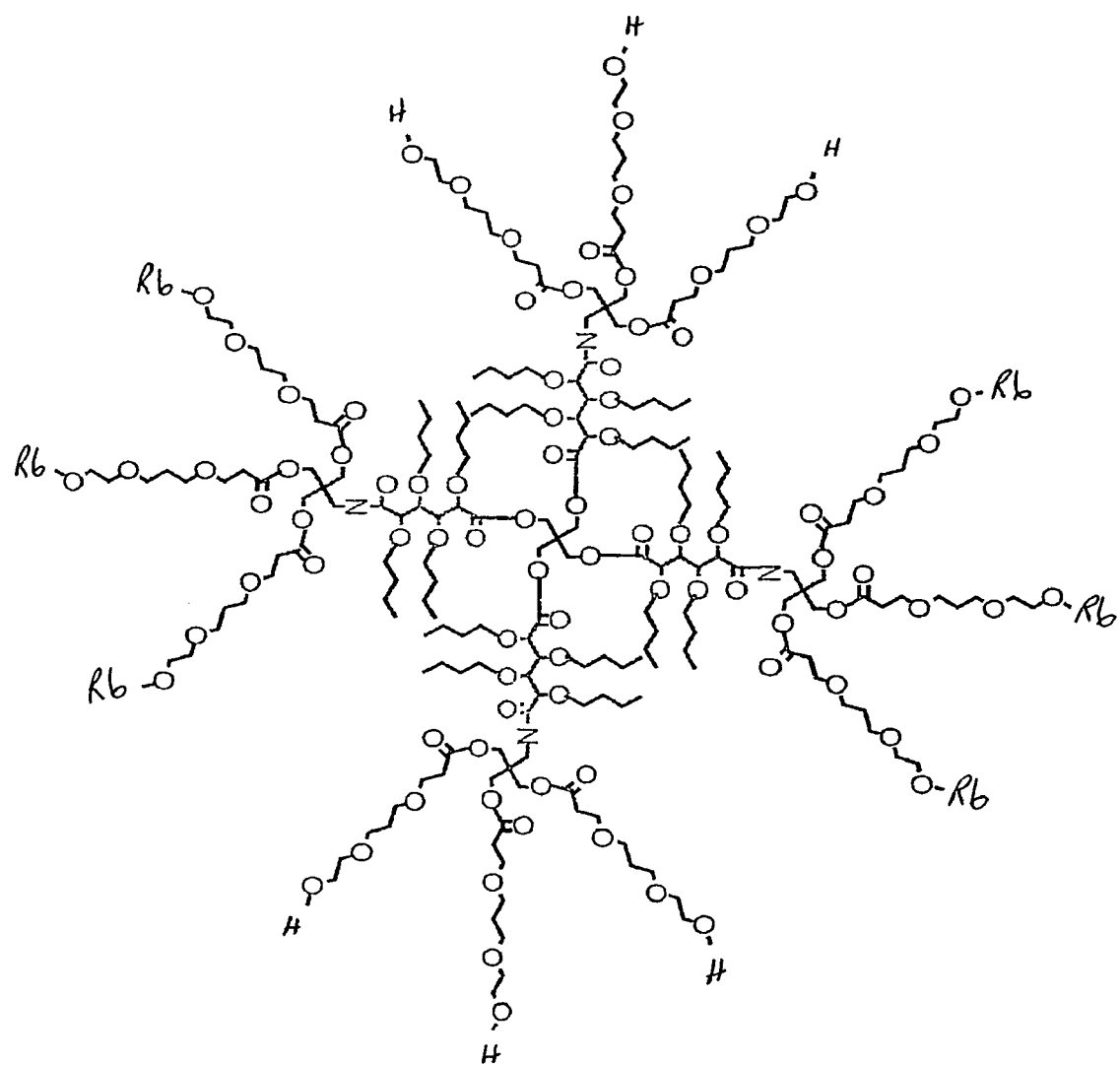

As used herein the term "polyol" includes straight chain and branched chain aliphatic groups, as well as mono-cyclic and poly-cyclic aliphatics, which are substituted with two or more hydroxy groups. A polyol typically has from about 2 carbons to about 20 carbons; preferably, from about 3 carbons to about 12 carbons; and more preferably from about 4 carbons to about 10 carbons. A polyol also typically comprises from about 2 to about 20 hydroxy groups; preferably from about 2 to about 12 hydroxy groups; and more preferably from about 2 to about 10 hydroxy groups. A polyol can also optionally be substituted on a carbon atom with one or more (e.g., 1, 2, or 3) carboxy groups (COOH). These carboxy groups can conveniently be used to link the polyol to the polyether in a compound of formula (I).

Polyols that are suitable for use as the polymer core are nearly limitless. Aliphatic polyols having from 1 to 10 carbon atoms and from 1 to 10 hydroxyl groups may be used, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, tlheitol, arabitol, erythritol, adonitol, dulcitol, fucose, ribose, arabinose, xylose, lyxose, rhanmose, galactose, glucose, fructose, sorbose, mannose, pyranose, altrose, talose, tagitose, pyranosides, sucrose, lactose, maltose, and the like. Additional examples of aliphatic polyols include derivatives of glyceraldehyde, glucose, ribose, mannose, galactose, and related stereoisomers.

Other $R^1$ polyols that may be used include cyclic crown ethers, cyclodextrines, dextrines and other carbohydrates such as starches and amylose. Alkyl groups may be straight-chained or branched, and may contain from 1 to 10 carbon atoms.

The term "polyacids" as used herein include compounds which have two or more acid groups per molecule. Preferably, the polyacid is a dibasic, tribasic or polybasic carboxylic acid functional compound. The polyacid can generally be aliphatic, cycloaliphatic or aromatic. Examples of polyacids include compound such as cyclodextrans and calerixane.

Specific $R^3$ groups are formed from di-carboxylic acids containing from 1 to about 10 carbon atoms and substituted with from 1 to about 10 hydroxyl groups. The mono-or di-carboxylic acid may be a straight chained or branched chained aliphatic, or a mono-cyclic or poly-cyclic aliphatic compound. Suitable dicarboxylic acids include mucic acid, malic acid, citromalic acid, alkylmalic acid, hydroxy derivatives of glutacic acid, and alkyl glutadc acids, tartadc acid, citric acid, hydroxy derivatives of rumadc acid, and the like. Suitable monocarboxylic acids include 2,2-(bis(hydroxymethyl)propionic acid, and N-[tris(hydroxymethyl)methyl] glycine (tricine).

Specific "sugar moieties" include monosaccharides, disaccharides, trisacharides, and polysaccharides. Non-limiting examples of sugar moieties include straight chained or closed-ring sugars and sugar alcohols, such as, for example, mannitol, sorbitol, inositol, xylitol, quebrachitol, tlreitol, arabitol, erythritol, adonitol, dulcitol, fucose, ribose, arabinose, xylose, lyxose, rhanmose, galactose, glucose, fructose, sorbose, mannose, pyranose, altrose, talose, tagitose, pyranosides, sucrose, lactose, maltose, and the like. Additional examples of aliphatic polyols include derivatives of glyceraldehyde, glucose, ribose, mannose, galactose, and related stereoisomers. Preferred sugar moieties are glucose, sucrose, fructose, ribose, and the like, and deoxy sugars such as deoxyribose, and the like. Saccharide derivatives can conveniently be prepared by methods known to the art. Examples of suitable mono-saccharides are xylose, arabinose, ribose, and the like. Examples of di-saccharides are maltose, lactose, sucrose, and the like. Examples of suitable sugar-alcohols are erythritol, sorbitol, and the like.

As used herein, the term polyether includes poly(alkylene oxides) having between about 2 and about 150 repeating units. Typically, the poly(alkylene oxides) have between about 50 and about 110 repeating units. The alkylene oxide units contain from 2 to 10 carbon atoms and may be straight chained or branched. Preferably, the alkylene oxide units contain from 2 to 10 carbon atoms. Poly(ethylene glycol) (PEG) is preferred. Alkoxy-, amino-, carboxy-, and sulfo-terminated poly(alkylene oxides) are preferred.

In a compound of formula (I), a poly(alkylene oxide) can be linked to a polyol, for example, through an ether, thio-ether, amine, ester, thioester, thioamide, or amide linkage. Preferably, a poly(alkylene oxide) is linked to $R^3$ by an ester or amide linkage in a compound of formula (I).

As used herein, the term polyimine includes poly(alkylene imines) having between about 2 and about 150 repeating units. Typically, the poly(alkylene imines) have between about 50 and about 110 repeating units. The alkylene imine units contain from 2 to 10 carbon atoms and may be straight chained or branched. Preferably, the alkylene imine units contain from 2 to 10 carbon atoms. Poly(ethylene imine) (PEI) is preferred. Alkoxy-, amino-, carboxy-, and sulfo-terminated poly(alkylene imines) are preferred.

In a compound of formula (I), a poly(alkylene imine) can be linked to a polyol, for example, through an ether, thio-ether, amine, ester, thioester, thioamide, or amide linkage. Preferably, a poly(alkylene imine) is linked to $R^3$ by an ester or amide linkage in a compound of formula (I).

As used herein, the term "targeting moiety" refers to groups that have an ability to direct the encapsulated active agents to a site where the activity from the active agent is desired. In the present invention the polymers can have one or more targeting moiety. Non-limiting examples of targeting moieties include but are not limited to groups such as, for example, $-CO_2H$, $-SO_3H$ (sulfo), $-NH_2$, or groups derived from compounds such as, for example, biotin, streptavidin, sugar moieties, folic acid, amino acids and peptides.

As used herein, the term fatty acid includes fatty acids and fatty oils as conventionally defined, for example, long-chain aliphatic acids that are found in natural fats and oils. Fatty acids typically comprise from about 2 to about 24 carbon atoms. Preferably, fatty acids comprise from about 6 to about 18 carbon atoms. The term "fatty acid" encompasses compounds possessing a straight or branched aliphatic chain and an acid group, such as a carboxylate, sulfonate, phosphate, phosphonate, and the like. The "fatty acid" compounds are capable of "esterifying" or forming a similar chemical linkage with hydroxy groups on the polyol. Examples of suitable fatty acids include caprylic, capric, lauric, myristic, myristoleic, palmitic, palmitoleic, stearic, oleic, linoleic, eleostearic, arachidic, behenic, erucic, and like acids. Fatty acids can be derived from suitable naturally occurring or synthetic fatty acids or oils, can be saturated or unsaturated, and can optionally include positional or geometric isomers. Many fatty acids or oils are commercially available or can be readily prepared or isolated using procedures known to those skilled in the art.

As used herein the term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g., as a $(C_1-C_6)$ alkyl, phenyl or benzyl ester or amide, or as an *-methyl-benzyl amide). Other suitable amino and carboxy protecting groups are known to those skilled in the art (See for example, T. W. Greene, *Protecting Groups In Organic Synthesis*; Wiley: New York, 1981, and references cited therein). An amino acid can be linked to the remainder of a compound of formula I through the carboxy terminus, the amino terminus, or through any other convenient point of attachment, such as, for example, through the sulfur of cysteine.

As used herein, the term "peptide" describes a sequence of 2 to 25 amino acids (e.g., as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

It is understood that in the compounds of the invention where $R^2$ is a polyvalent moiety one valence is attached to $R^1$ and each of the other valences is attached to a group having the formula $-(R^3)_b-(R^4)_c-(R^5)_d-(R^6)_e$ where each $R^3$, $R^4$, $R^5$, $R^6$, b, c, d, and e independently have the meanings described herein above.

It is understood that in the compounds of the invention where $R^4$ is a polyvalent moiety one valence is attached to $R^3$ and each of the other valences is attached to a group having the formula $-(R^5)_d-(R^6)_e$ where each $R^5$, $R^6$, d, and e independently have the meanings described herein above.

As used herein, a "cross-linked macromolecule" means a micelle that has been cross-linked to provide a covalently cross-linked structure.

As used herein, the term "encapsulate" means a composition, having a molecule (e.g., a therapeutic agent) surrounded or partially surrounded by at least one compound of formula (I). The term encapsulate includes structures wherein the compound of formula (I) has been cross-linked, as well as structures wherein the compound of formula (I) has not been cross-linked.

The compounds of formula (I) that comprise unsaturated bonds can be cross-linked to form more stabilized polymers, which comprise a compound of formula (I) that have been covalently linked.

Typically, the polymers of the invention have a diameter of from about 10 nm to about 1000 nm. The diameters can be measured using any suitable analytical technique, such as, for example, dynamic light scattering.

Compounds of formula (I) can be used for drug solubilization, fragrance encapsulation, passive and active targeting for drug delivery, waste water treatment, enhanced capillary electrophoresis activation, and induction of protein crystallization.

Accordingly, as used herein, the term "molecule" includes any compound that can be incorporated into a polymer or a cross-linked polymer as described herein. Typically, "molecules" have solubility properties that are undesirable and that can be modified by incorporation into an amphiphilic polymer or a cross-linked polymer of the invention. For example, the term "molecule" includes therapeutic agents, insecticides, pesticides, herbicides, antiseptics, food additives, fragrances, dyes, diagnostic aids, and the like. Other specific examples of molecules include, but are not limited to:

abietic acid, aceglatone, acenaphthene, acenocoumarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allyl sulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, astemizole, aurodox, aurothioglycamide, 8-azaguanine, azobenzene;

baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bomyl, bromoisovalerate, bomyl chloride, bomyl isovalerate, bomyl salicylate, brodifacoum, bromethalin, broxyquinoline, bufexamac, butaunirate, butethal, buthiobate, butlated hydroxyanisole, butylated hydroxytoluene;

calcium iodostearate, calcium saccharate, calcium stearate, capobenic acid, captan, carbamazepine, carbocloral, carbophenothin, carboquone, carotene, carvacrol, cephaeline, cephalin, chaulmoogfic acid, chenodiol, chitin, chlordane, chlorfenac, chlorfenetbol, chlorothalonil, chlorotrianisene, chlorprothixene, chlorquinaldol, chromonar, cilostazol, cinchonidine, citral, clinofibrate, clofazimine, clofibrate, cloflucarban, cionitrate, clopidol, clorindione, cloxazolam, coroxon, corticosterone, coumachlor, coumaphos, coumithoate cresyl acetate, crimidine, criformate, cuprobam, cyameniazine, cyclandelate, cyclarbamate cymarin, cypennethril;

dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicmarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicofinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscomacetate, ethylhydrocupreine, ethyl menthane carboxamide, eugenol, euprocin, exalamide;

febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furfuryl-5-isopropylbarbitufic acid, fusafungine, glafenine, glucagon, glutethimide, glybuthiazole, griseofulvin, guaiacol carbonate, guaiacol phosphate, halcinonide, hematoprphyrin, hexachlorophene, hexestrol, hexetidine, hexobarbital, hydrochlorothiazide, hydrocodone, ibuproxam, idebenone, indoomethacin, inositol niacinate, iobenzamic acid, iocetamic acid, iodipamide, iomegiamic acid, ipodate, isomeptene, isonoxin, 2-isovalerylindane-1,3-dione;

josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, mielarsoprol, melphalan, menadione, menthyl valerate, mephenoxalone, mephentennine, mephenyloin, meprylcaine, mestanolone, mestranol, mesulfen, metergoline, methallatal, methandriol, methaqualone, 3-methylcholanthrene, methylphenidate, 17-methyltestosterone, metipranolol, minaprine, myoral, nafialofos, nafiopidil, naphthalene, 2-naphthyl lactate, 2-(2-naphthyloxy)ethan01, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone;

octavefine, oleandrin, oleic acid, oxazepam, oxazolam, oxelandin, oxwthazaine, oxycodone, oxymesterone, oxyphenistan acetate, paclitaxel, paraherquamide, parathion, pemoline, pentaerythritol tetranitrate, pentylphenol, perphenazine, phencarbamide, pheniramine, 2-phenyl-6-chlorophenol, phentlmethylbarbituric acid, phenyloin, phosalone, pbthalylsulfathiazole, phylloquinone, picadex, pifamine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate;

quercetin, quinbolone, quizalofo-ethyl, rafoxamide, rescinnamine, rociverine, ronnel salen, scarlet red, siccmn, simazine, simetfide, sobuzoxanie, solan, spironolactone, squalene, stanolone, sucralfate, sulfabenz, sulfaguanole, sulfasalazine, SUlfoxide, sulpiride, suxibuzone, talbutal, terguide, testosterone, tetrabromocresol, tetrandrine, thiacetazone, thiocoichicine, thiocftc acid, thioquinox, thioridazine, thiram, thymyl N-isoamylcarbamate, tioxidazole, tioxolone, tocopherol, tolciclate, tolnafiate, triclosan, triflusal, triparanol;

ursolic acid, valinomycin, verapamil, vinblastine, vitamin A, vitamin D, vitamin E, xenbucin, xylazine, zaltoprofen, and zearalenone.

A specific polyacid moiety includes compounds having the formula

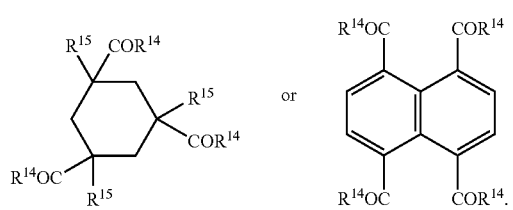

A specific $R^{15}$ is alkyl.
A more specific $R^{15}$ is methyl, ethyl, or propyl.
A more specific $R^{15}$ is methyl, or propyl.
A specific polyol has the formula:

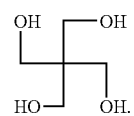

Specific $R^2$ groups are derived from compounds having the formula:

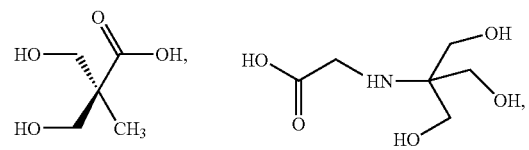

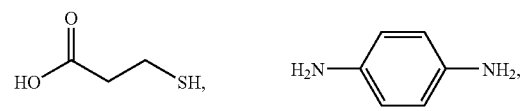

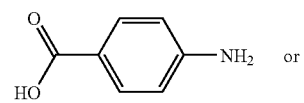

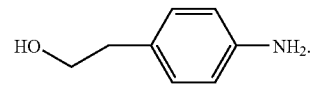

More specific $R^2$ groups are derived from compounds having the formula:

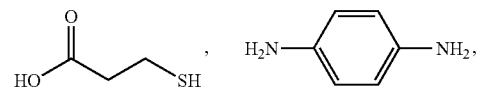

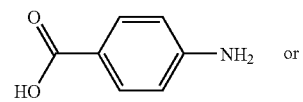

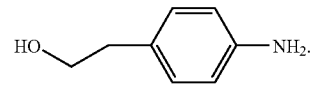

A Specific $R^2$ groups has the formula:

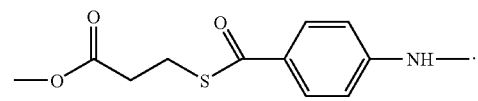

A specific $R^1$-$R^2$ combination is pentaerythritol tetrakis (3-mercapto-propionate) having the formula:

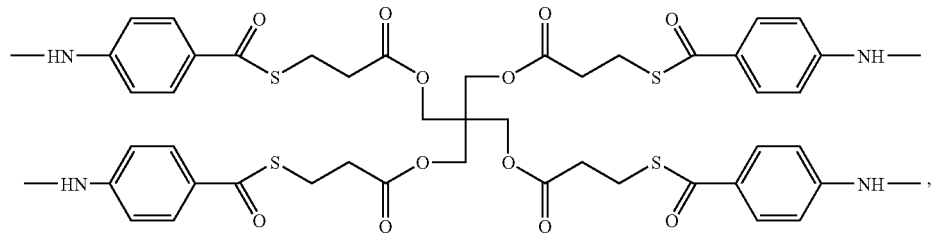

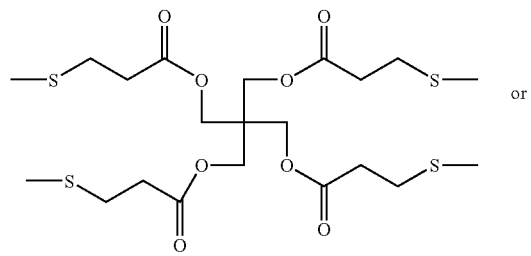 or 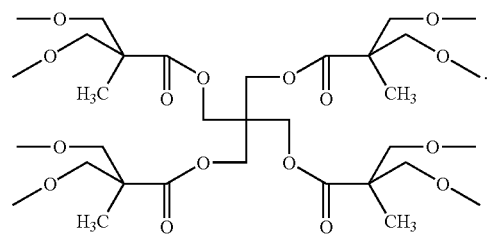

A specific R³ group has the formula

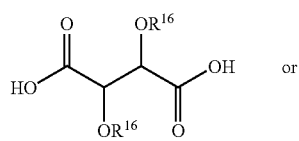 or

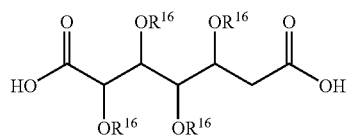

wherein each R¹⁶ is an alkanoyl group having from 2 to about 24 carbon atoms.

A specific R¹⁶ group is an alkanoyl group having from about 6 to about 18 carbon atoms.

A more specific R¹⁶ group is an alkanoyl group having from about 8 to about 12 carbon atoms.

A more specific R³ group is

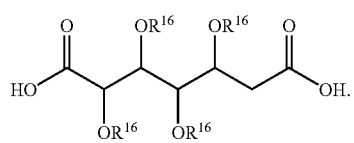

Specific R⁴ groups are derived from compounds having the formula:

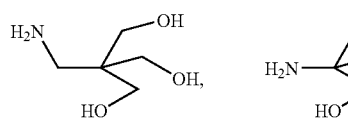

-continued

[structure with OH groups and H₂N]

Specific R⁵ groups are polyethylene ethers or polyethylene imines.

Specific polyethylene ethers have arcylene oxide units containing from 2 to about 10 carbon atoms.

Other specific polyethylene ethers have the formula —(O—CH₂—CH₂)$_f$— where f is an integer from about 2 to about 150.

More specific polyethylene ethers have the formula —(O—CH₂—CH₂)$_f$— where f is an integer from about 50 to about 110.

Specific polyethylene imines have units containing from 2 to about 10 carbon atoms.

Other specific polyethylene imines have the formula —(N(R⁷)—CH₂—CH₂)$_f$— where f is an integer from about 2 to about 150.

More specific polyethylene imines have the formula —(N(R⁷)—CH₂—CH₂)$_f$— where f is an integer from about 50 to about 110.

Specific R⁶ group is an alkyl or aryl groups, biotin, streptavidin, sugar moieties, folic acid, amino acids and a peptides.

A more specific R⁶ groups is the peptide Arg-Gly-Asp (R-G-D) or Tyr-Ile-Gly-Ser-Arg (Y—I-G-S—R).

A more specific R⁶ group is biotin.

The compounds of the invention can be prepared using procedures known to those skilled in the art. A representative synthesis is illustrated in Scheme 1, below.

SCHEME 1

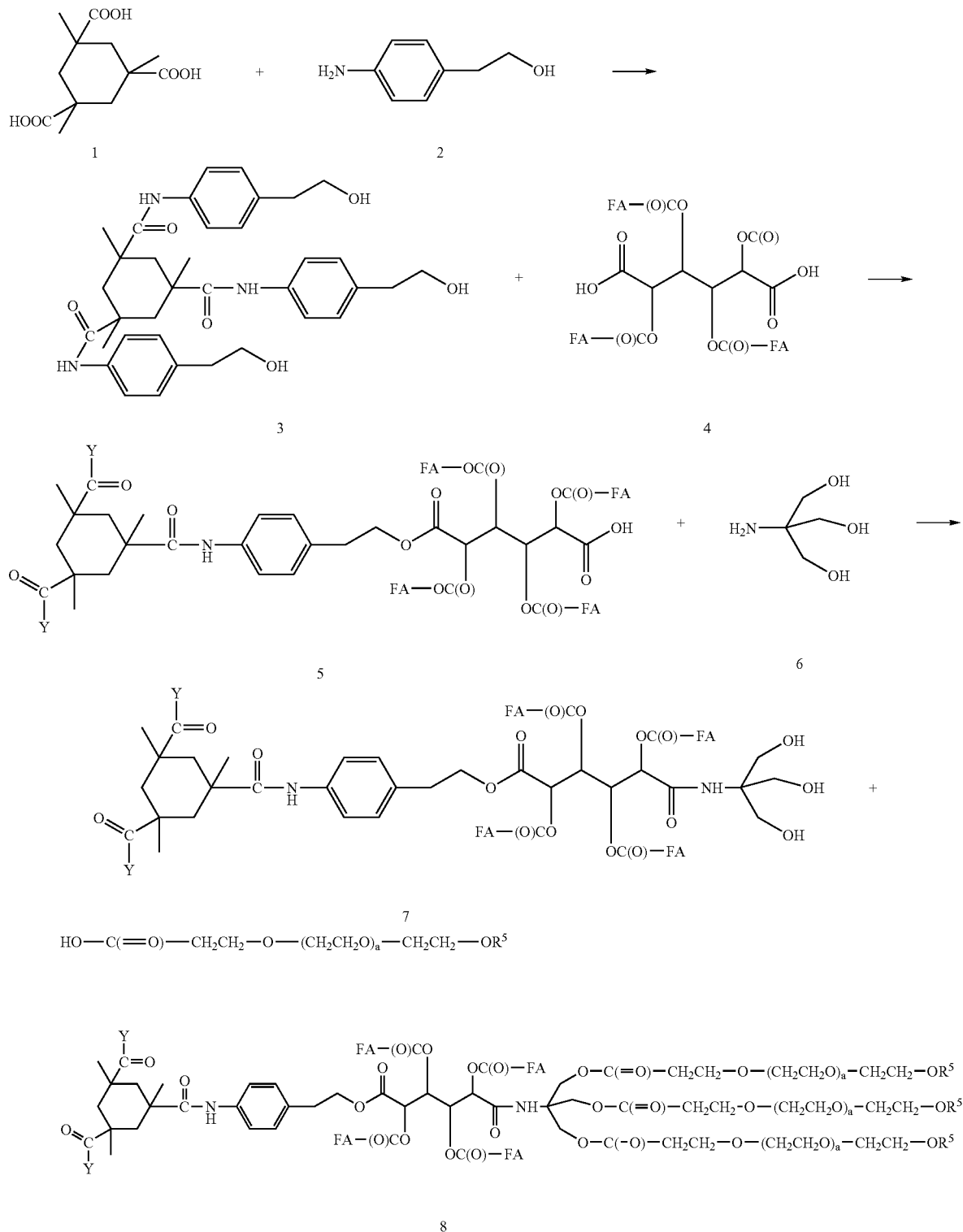

Triacid, 1, is reacted with three equivalents of 2-(4-aminophenyl)-ethanol, 2, in the presence of a coupling agent, dicyclocarbdiimide (DCC), to provide the tri-amide triol, 3. the triol is reacted with Mucic acid fatty acid ester (FA=a fatty acid residue) to provide acid, 5. (Each Y represents the corresponding group after completion of each reaction step.) Acid, 5, is reacted with amine triol, 6, by activation of the carboxylic acid with DCC, to provide triol amide, 7. Amide, 8, is reacted with a hydrophilic group such as, a polyethylene or a polyethylene imine to provide the macromolecule, 8.

Schemes 2 and 2A illustrate the preparation of the acylated compounds for use in $R^3$, the hydrophobic portion of the compounds of the invention. The acids are reacted with an acyl halide, (e.g., $CH_3$—$(CH_2CH_2)_nC(=O)Cl$, where m is from 2 to about 8) to provide the polyacylated products. Alternatively, the acyl halide, (e.g., $CH_3$—$(CH_2CH_2)_nC(=O)Cl$, or $CH_2=CH$—$(CH_2CH_2)_pC(=O)Cl$, where m is from 2 to about 8) is reacted with the acid in the presence of pyridine to provide the polyacylated compounds.

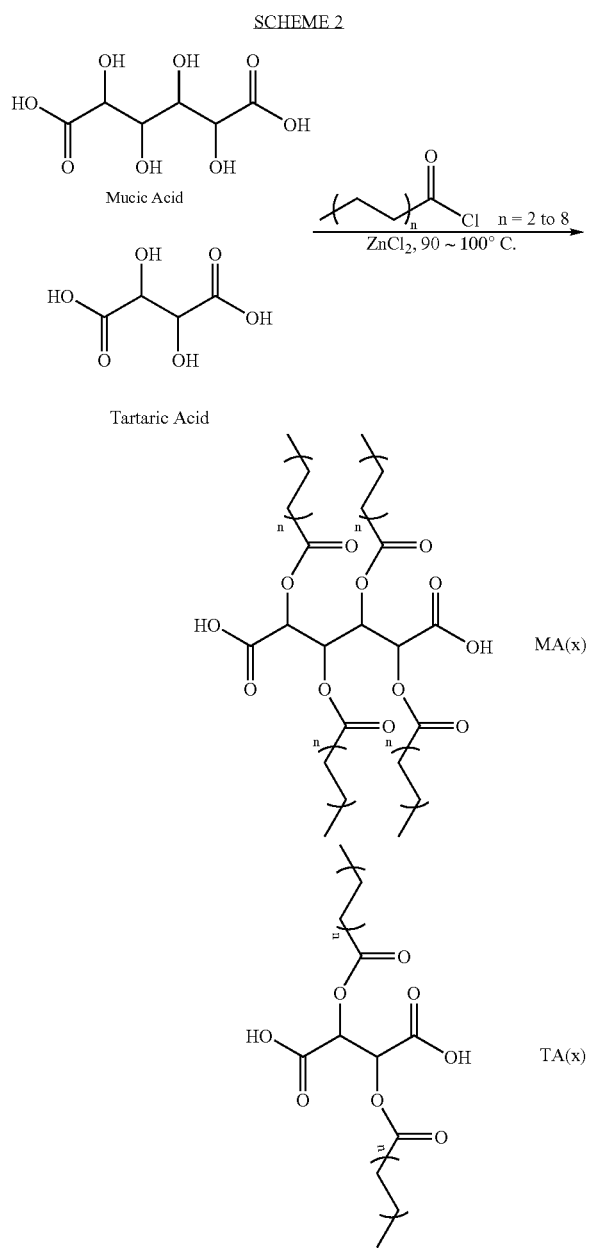

The macromolecules of the invention are particularly useful for solubilizing hydrophobic molecules, particularly therapeutic agents that are hydrophobic in nature. Thus, according to one embodiment of the present invention, a therapeutic agent is encapsulated by combining the agent and a plurality of compounds of formula (I) in a solvent, such as water. If the macromolecule has unsaturated groups, the compounds of formula (I) can be cross-linked to provide an encapsulate of the invention wherein the therapeutic agent is encapsulated in a cross-linked macromolecule.

The encapsulates of the invention that comprise a therapeutic agent can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the encapsulates of the invention may be systemically administered, e.g., orally, in combination with a pharmaceutically acceptable vehicle such as an inert diluent. They may be incorporated directly with the food of the patient's diet. For oral therapeutic administration, the encapsulates of the invention may be used in the form of elixirs, syrups: and the like.

The compositions may also contain a sweetening agent such as sucrose, fructose, lactose or aspartame or a flavoring agent such as peppermint, oil of wintergreen, or cherry flavoring may be added. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the encapsulates of the invention may be incorporated into sustained-release preparations and devices.

The encapsulates of the invention may also be administered intravenously or intraperitoneally by infusion or injection. Solutions of the encapsulates can be prepared, for example, in water. Under ordinary conditions of storage and use, these preparations may contain a preservative to prevent the growth of microorganisms.

The pharmaceutical dosage forms suitable for injection or infusion should be sterile, fluid and stable under the conditions of manufacture and storage. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the encapsulates of the invention in the required amount in the appropriate solvent with various of the other ingredients enumerated above, as required, followed by sterilization.

Encapsulation of molecules according to the invention modifies transdermal delivery of the molecule. Absorption through the skin can be increased or decreased by a factor of up to about 1000. Thus, the pharmaceutical dosage forms of present invention include dosage forms suitable for transdermal delivery, which, in addition to aqueous solutions, also include aqueous gels. The dosage form may be applied directly to the skin as a lotion, cream or salve, or a transdermal drug delivery device such as a transdermal patch may be employed, in which the encapsulated molecule is retained in the active agent reservoir of the patch.

The dose and method of administration will vary from animal to animal and be dependent upon such factors as the type of animal being treated, its sex, weight, diet, concurrent medication, overall clinical condition, the particular therapeutic agent employed, the specific use for which the agent is employed, and other factors which those skilled in the relevant field will recognize.

Therapeutically effective dosages may be determined by either in vitro or i) vivo methods. For each particular dosage form of the present invention, individual determinations may be made to determine the optimal dosage required. The range of therapeutically effective dosages will naturally be influenced by the route of administration, the therapeutic objectives, and the condition of the patient. The determination of effective dosage levels, that is, the dosage levels necessary to achieve the desired result, will be within the ambit of one skilled in the art. Typically, applications of agent are commenced at lower dosage levels, with dosage levels being increased until the desired effect is achieved.

A typical dosage might range from about 0.001 mg to about 1,000 mg of therapeutic agent, per kg of animal weight. Preferred dosages range from about 0.01 mg/kg to about 100 mg/kg, and more preferably from about 0.10 mg/kg to about 20 mg/kg. Advantageously, the dosage forms of this invention may administered several times daily, and other dosage regimens may also be useful.

The compounds of formula (I), of the invention may also be used as thickening agents, lubricants, detergents surfactants, plasticizers and anti-fouling agents. The compounds of formula (I), of the invention may be used as an emulsifying, dispersing or stabilizing agent for dyes, cosmetics, pigment and pharmaceutical products. The compounds of formula (I), of the invention are particularly useful as an, emulsifying, dispersing or stabilizing agent in the dyeing of textiles and for encapsulating dyes for cosmetics. The compounds of formula (I), of the invention are useful as lubricants and as a thickening agents for paints. The compounds of formula (I), of the invention may also be employed as an emulsifying, dispersing or stabilizing agent for components of photographic compositions and developers.

For therapeutic applications, the preferred polymers of the invention hydrolyze into components known to be biocompatible, e.g., sugars, fatty acids, amino acids and poly(ethylene glycol). This also results in low cytotoxicity of the polymer and its hydrolysis products. The poly(alkylene oxide) units enhance the immunogenicity of the encapsulate, enabling the hydrophobic molecules to evade the body's immune system, thereby increasing the circulation time of the hydrophobic molecule. This allows for effective treatment with reduced quantities of the hydrophobic molecule, which, together with the enhanced immunogenicity, prevents or reduces the severity of incidents of toxic side effects.

The following non-limiting examples set forth hereinbelow illustrate certain aspects of the invention. All parts and percentages are by weight unless otherwise noted and all temperatures are in degrees Celsius.

All PEG's were obtained from Shearwater Polymers (Birmingham, Ala.) and used without further purification. All other chemicals were obtained from Aldrich (Milwaukee, Wis.), and used without further purification. Analytical grade solvents were used for all the reactions. Methylene chloride, tetrahydrofuran (THF), triethylamine (TEA) and dimethylsulfoxide (DMSO) were distilled. 4-(dimethylamino)pyridinium p-toluenesulfonate (DPTS) was prepared as described by J. S. Moore, S. I. Stupp *Macromolecules* 1990, 23, 65. $^1$H-NMR and spectra were recorded on a Varian 200 MHz or 400 MHz spectrometer. Samples (~5-10 mg/ml) were dissolved in CDCl$_3$ or THF-d$_4$, with the solvent used as an internal reference. IR spectra were recorded on a Mattson Series spectrophotometer by solvent casting samples onto a KBr pellet. Thermal analysis data were determined on a Perkin-Elmer Pyris 1 DSC system, samples (~10 mg) were heated under dry nitrogen gas. Data were collected at heating and cooling rates of 5° C./min. Gel permeation chromatography (GPC) was performed on a Perkin-Elmer Series 200 LC system. Dynamic laser scattering (DSL) measurements were carried on NICOMP particle sizing systems.

EXAMPLES

Examples 1-3

Acylation of Mucic Acid

Example 1

Mucic Acid Propyl Ester

To a neat mixture of mucic acid (4.2 g, 20 mmol) and propionyl chloride (18 ml, 200 mmol) was added ZnCl$_2$ (0.28 g, 2.0 mmol). The reaction mixture was heated at reflux temperature for three hours. After cooling, diethyl ether (20 ml) was added to the reaction mixture and the solution poured onto ice chips (approximately 100 g) with stirring. Additional diethyl ether (80 ml) was added to the mixture and stirring continued for 30 minutes more. The ether portion was separated, washed with water to a neutral pH, dried over anhydrous Na$_2$SO$_4$ and evaporated to dryness. The crude product was purified by recrystallization from a cosolvent system of diethyl ether and methylene chloride, collected by vacuum filtration, washed by ice cold methylene chloride and dried at 105° C. (12 hours) to constant weight. A white solid having a T$_m$, of 196° C. was obtained at a 56% yield.

Example 2

Mucic Acid Hexyl Ester

Mucic acid hexyl ester was prepared as in Example 1, substituting caproyl chloride for propionyl chloride. A white solid having a T$_m$ of 171° C. was obtained at a yield of 68%.

Example 3

Mucic Acid Lauryl Ester

Mucic acid lauryl ester was prepared as in Example 1, substituting lauryl chloride for propionyl chloride. A white solid having a T$_m$ of 145° C. was obtained at a yield of 65%.

Examples 4-6

Preparation of Polymer Core

Example 4

Propyl Ester

The mucic acid propyl ester of Example 1(6.0 mmol) and 1,1,1-tris(4'-hydroxyphenyl)ethane (0.51 g, 1.7 mmol) were dissolved in anhydrous ethyl ether (150 ml). To the reaction mixture, a solution of DCC (1.2 g, 6.0 mmol) and DMAP (0.74 g, 6.0 mmol) in 25 ml methylene chloride was added dropwise. After 15 minutes, the DCC side-product (dicyclohexylurea) was removed by suction filtration. The filtrate was washed with 20 ml portions of 0.1 N HCL (2×) and brine (4×), dried over anhydrous Na$_2$SO$_4$, and evaporated to dryness. The crude product was purified by flash chromatography using ethyl ether: methanol: acetic acid (90:5:5) as eluent. A white solid having a $T_m$ of 158° C. was obtained at 58% yield.

Example 5

Hexyl Ester

The hexyl ester core molecule was prepared according to the method of Example 4, substituting the mucic acid hexyl ester of Example 2 for the mucic acid propyl ester. A white solid having a $T_m$ of 147° C. was obtained at 36% yield.

Example 6

Lauryl Ester

The lauryl ester core molecule was prepared according to the method of Example 4, substituting the mucic acid lauryl ester of Example 3 for the mucic acid propyl ester. A white solid having a $T_m$ of 136° C. was obtained at yield of 33%.

Examples 7-11

Preparation of Final Polymers

Example 7

Mucic Acid Hexyl Ester Core Polymer with Triethylene Glycol (TEG) Branches

To a mixture of the core molecule of Example 5 (0.106 mmol) and methoxy-terminated triethylene glycol amine (0.351 mmol) in 20 ml of methylene chloride at room temperature, DCC (0.351 mmol) and DMAP (0.351 mmol) in 2 ml methylene chloride was added dropwise. After three days, the reaction mixture was evaporated to dryness, the residue dissolved into 20 ml methanol, and the crude product precipitated from 400 ml petroleum ether at room temperature. The crude product was first purified by flash chromatography using ethyl ether: methanol: acetic acid (90:5:5) as eluent, then further purified by repetitive precipitation using methylene chloride as solvent and diethyl ether/petroleum ether as non-solvent. The ratio between methylene chloride and ethers was progressively changed. A white solvent was obtained having a $T_m$ of 31° C., a $T_d$ of 220° C. and $M_W$ of 2,400 daltons at a yield of 15%.

Example 8

Mucic Acid Hexyl Ester Core Polymer with PEG 2000 Branches

A mucic acid hexyl ester core polymer with PEG 2000 branches was prepared according to the method of Example 7, substituting methoxy-terminated poly(ethylene glycol) amine (H$_2$N-m-PEG 2000, $M_w$=2000) for the methoxy-terminated triethylene glycol amine of Example 7. A white solid was obtained having a $T_m$ of 54° C. and a $M_w$ of 9,400 daltons at a yield of 25%.

Example 9

Mucic Acid Hexyl Ester Core Polymer with PEG 5000 Branches

A mucic acid hexyl ester core polymer with PEG 5000 branches was prepared according to the method of Example 7, substituting methoxy-terminated poly(ethylene glycol) amine (H$_2$N-PEG 5000, $M_w$=5000) for the methoxy-terminated triethylene glycol amine of Example 7. A white solid having a $T_m$ of 61° C. and a $M_w$ of 17,800 daltons was obtained at 17% yield.

Example 10

Mucic Acid Propyl Ester Core Polymer with PEG 5000 Branches

Mucic acid propyl ester core polymer with PEG 5000 branches was prepared according to the method of Example 9, substituting the mucic acid propyl ester core polymer of Example 4 for the mucic acid hexyl ester core polymer. A white solid was obtained having a $T_m$ of 62° C. and a $M_w$ of 17,000 daltons at 30% yield.

Example 11

Mucic Acid Lauryl Ester Core Polymer with PEG 5000 Branches

Mucic acid lauryl ester core polymer with PEG 5000 branches was prepared according to the method of Example 9, substituting the mucic acid lauryl ester core polymer of Example 6 for the mucic acid hexyl ester core polymer. A white solid was obtained having a $T_m$ of 60° C. and a $M_w$ of 19,100 daltons at a yield of 45%.

For the polymers of Examples 8-11, TGA showed two stages of decomposition. The first stage corresponded to cleavage of the core structures from the ethylene oxide chains (about 200° C.) with the appropriate weight loss, and the second stage corresponded to decomposition of the ethylene oxide chain.

Example 12

Encapsulation Studies

Lidocaine (50 mg) and the polymer of Example 9 (50 mg) were dissolved in 2.0 ml methylene chloride. The solution was evaporated to dryness and the solid residue extensively washed with hexane until lidocaine was no longer detected in the washings. The solid was dried under vacuum at 25° C. for about 2 hours. A portion (5.0 mg) of this solid was dissolved into methanol (1.0 ml) to release the entrapped lidocaine, and the lidocaine concentration was quantified by high pressure liquid chromatography (HPLC) according to a calibration curve generated from a series of standard solutions ranging from 0.005 to 0.5 mg/ml lidocaine. The linearity of the curve indicated a direct, proportional relationship between absorbance and lidocaine concentration. Using the equation of the lidocaine calibration curve, the amount of lidocaine entrapped in the unimolecular micelle core was determined. PEG with a molecular weight of 5,000 daltons was used as the HPLC control.

Encapsulation number was defined as the amount of molecules that can be entrapped within the polymeric micelles. The values for the polymers of Example 9, 10 and 11 were 1.0, 0.7 and 1.6 weight %, respectively. The encapsulation number increased as the hydrophobicity of the polymer interior increased.

The PEG arms of the polymers of the present invention thus form a hydrophilic shell that solubilizes the polymer in water, while the core forms a hydrophobic microenvironment that encapsulates small hydrophobic molecules. Unlike conventional micelles, however, the polymeric micelles of the present invention are thermodynamically stable because of the covalent linkages between the polymer arms. The ability to encapsulate small molecules, the enhanced solubility and the lack of aggregation characterize the usefulness of these polymers as drug delivery systems. Candidate drugs, of which there are many, have aromatic or heteroaromatic moieties and carbonyl functionalities (e.g., amides and carboxylates). The biocompatibility and biodegradability of these polymers further characterize their utility for drug delivery. The excellent water-solubility of these polymers makes intravenous injection and oral administration of hydrophobic drug molecules possible. For controlled release applications, the small size of these polymers, along with their enhanced thermodynamic stability, further characterizes their utility.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The invention claimed is:

1. A compound having formula (I):

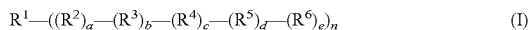

wherein $R^1$ is a core comprising a polyol or polyacid;

each $R^2$ independently is a divalent or polyvalent group having the formula $-X^1-R^8-(X^{1a})_g-$, wherein $X^1$ and $X^{1a}$ are independently $-C(=O)-$, $-C(=S)-$, $-O-$, $-S-$, $-N(R^7)-$ or absent, and each $R^8$ is independently $-(C_{1-8})$alkylene-, branched $-(C_{1-8})$alkylene- or $-(C_{6-10})$aryl-; a is 0 or an integer from 1 to about 10; and g is an integer from 1 to about 6;

each $R^3$ independently is a divalent dicarboxylic acid moiety having the formula $-C(=O)-R^9-C(=O)-$, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula $-X^2-R^{10}-(X^{2a})_h-$, wherein $X^2$ is $-C(=O)-$, $-C(=S)-$, $-O-$, $-S-$, $-N(R^7)-$ or absent; $X^{2a}$ is $-C(=O)-$, $-C(=S)-$, $-O-$, $-S-$, or $-N(R^7)-$ and $R^{10}$ is $-(C_{1-8})$alkylene-, branched $-(C_{1-8})$alkylene- or $-(C_{6-10})$aryl-; and c is 0 or an integer from 1 to about 10; and h is an integer from 1 to 6;

each $R^5$ independently is a group having the formula:

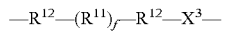

wherein $R^{11}$ is a sugar moiety; or a poly(alkylene oxide) or poly(alkylene imine) group having the formula $-(-X^4-R^{13})-$; wherein $R^{13}$ is $-(C_{2-40})$alkylene- or branched $-(C_{3-40})$alkylene-; wherein each $X^3$ is independently $-C(=O)-$, $-C(=S)-$, $-O-$, $-S-$, $-N(R^7)-$ or absent; and f is an integer from about 2 to about 150; and d is from 1 to about 6;

each $R^{12}$ is independently a bond, $-(C_{1-40})$alkylene- or branched $-(C_{1-40})$alkylene-groups, wherein each $R^{12}$ is optionally substituted with one or more (e.g., 1, 2, or 3) functional groups; and $X^4$ is $-O-$, $-S-$, or $-N(R^7)-$;

wherein n is from 2 to 12; provided that a and b are not both zero; wherein each $R^7$ is independently selected from the group consisting of hydrogen, and $C_{(1-40)}$ alkyl group, where the alkyl group can be a straight-chain or branched group; and $R^a$ and $R^b$ are each independently hydrogen $(C_{1-8})$alkyl, aryl, aryl$(C_{1-8})$alkylene; and $R^6$ is hydrogen, $-OH$, $-OR^a$, $-NR^aR^b$, $-CO_2H$, $-SO_3H$ (sulfo), $-CH_2-OH$, $-CH_2-OR^a$, $-CH_2-O-CH_2-R^a$, $-CH_2-NR^aR^b$ or a targeting moiety; provided that at least one $R^6$ group is a targeting moiety selected from $-CO_2H$, $-SO_3H$ (sulfo), $-NH_2$, biotin, streptavidin, a sugar moiety, folic acid, an amino acid and a peptide; and e is from 1 to about 6.

2. A compound having formula (I):

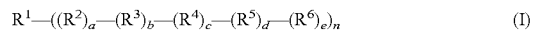

wherein $R^1$ is a core comprising a polyol or polyacid;

each $R^2$ independently is a divalent or polyvalent group having the formula $-X^1-R^8-(X^{1a})_g-$, wherein $X^1$ and $X^{1a}$ are independently $-C(=O)-$, $-C(=S)-$, $-O-$, $-S-$, $-N(R^7)-$ or absent, and each $R^8$ is independently $-(C_{1-8})$alkylene-, branched $-(C_{1-8})$alkylene- or $-(C_{6-10})$aryl-; a is an integer from 1 to about 10; and g is an integer from 1 to about 6;

each $R^3$ independently is a divalent dicarboxylic acid moiety having the formula $-C(=O)-R^9-C(=O)-$, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula $-X^2-R^{10}-(X^{2a})_h-$, wherein $X^2$ is $-C(=O)-$, $-C(=S)-$, $-O-$, $-S-$, $-N(R^7)-$ or absent; $X^{2a}$ is $-C(=O)-$, $-C(=S)-$, $-O-$, $-S-$, or $-N(R^7)-$ and $R^{10}$ is $-(C_{1-8})$alkylene-, branched $-(C_{1-8})$alkylene- or $-(C_{6-10})$aryl-; and c is 0 or an integer from 1 to about 10; and h is an integer from 1 to 6;

each $R^5$ independently is a group having the formula:

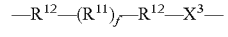

wherein $R^{11}$ is a sugar moiety; or a poly(alkylene oxide) or poly(alkylene imine) group having the formula $-(-X^4-R^{13})-$; wherein $R^{13}$ is $-(C_{2-40})$alkylene- or branched $-(C_{3-40})$alkylene-; wherein each $X^3$ is independently $-C(=O)-$, $-C(=S)-$, $-O-$, $-S-$, $-N(R^7)-$ or absent; and f is an integer from about 2 to about 150; and d is from 1 to about 6;

each $R^{12}$ is independently a bond, $-(C_{1-40})$alkylene- or branched $-(C_{1-40})$alkylene-groups, wherein each $R^{12}$ is optionally substituted with one or more (e.g., 1, 2, or 3) functional groups; and $X^4$ is $-O-$, $-S-$, or $-N(R^7)-$;

wherein n is from 2 to 12; provided that a and b are not both zero; wherein each $R^7$ is independently selected from the group consisting of hydrogen, and $C_{(1-40)}$ alkyl group, where the alkyl group can be a straight-chain or branched group; and $R^a$ and $R^b$ are each independently hydrogen $(C_{1-8})$alkyl, aryl, aryl$(C_{1-8})$alkylene; and $R^6$ is hydrogen, —OH, —$OR^a$, —$NR^aR^b$, —$CO_2H$, —$SO_3H$ (sulfo), —$CH_2$—OH, —$CH_2$—$OR^a$, —$CH_2$—O—$CH_2$—$R^a$, —$CH_2$—$NR^aR^b$ or a targeting moiety; and e is from 1 to about 6.

3. A compound having the formula

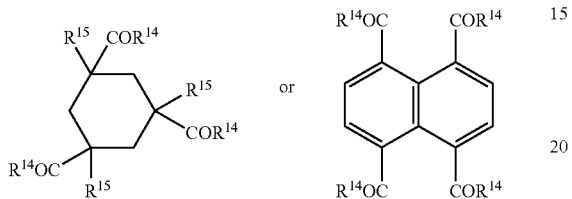

or a pentaerythritol polyol having the formula

wherein each $R^{14}$ is —$(R^2)_a$—$(R^3)_b$—$(R^4)_c$—$(R^5)_d$—$(R^6)_e$; and wherein $R^{15}$ is hydrogen or $(C_{1-6})$alkyl;

wherein each $R^2$ independently is a divalent or polyvalent group having the formula —$X^1$—$R^8$—$(X^{1a})_g$—, wherein $X^1$ and $X^{1a}$ are independently —C(=O)—, —C(=S)—, —O—, —S—, —N($R^7$)— or absent, and each $R^8$ is independently —$(C_{1-8})$alkylene-, branched —$(C_{1-8})$alkylene- or —$(C_{6-10})$aryl-; a is 0 or an integer from 1 to about 10; and g is an integer from 1 to about 6;

each $R^3$ independently is a divalent dicarboxylic acid moiety having the formula —C(=O)—$R^9$—C(=O)—, wherein $R^9$ is an alkylene or cycloalkylene group containing from 1 to about 15 carbon atoms, substituted with a total of from 1 to about 10 hydroxy groups, wherein one or more of the hydroxy groups of the dicarboxylic acid are acylated with an acid residue; and b is an integer from 1 to about 10;

each $R^4$ independently is a divalent or polyvalent group having the formula —$X^2R^{10}(X^{2a})_h$—, wherein $X^2$ is —C(=O)—, —C(=S)—, —O—, —S—, —N($R^7$)— or absent; $X^{2a}$ is —C(=O)—, —C(=S)—, —O—, —S—, or —N($R^7$)— and $R^{10}$ is —$(C_{1-8})$alkylene-, branched —$(C_{1-8})$alkylene- or —$(C_{6-10})$aryl-; and c is 0 or an integer from 1 to about 10; and h is an integer from 1 to 6;

each $R^5$ independently is a group having the formula:

—$R^{12}$—$(R^{11})_f$—$R^{12}$—$X^3$— wherein $R^{11}$ is a sugar moiety; or a poly(alkylene oxide) or poly(alkylene imine) group having the formula —$(-X^4-R^{13})$—; wherein $R^{13}$ is —$(C_{2-40})$alkylene- or branched —$(C_{3-40})$alkylene-; wherein each $X^3$ is independently —C(=O)—, —C(=S)—, —O—, —S—, —N($R^7$)— or absent; and f is an integer from about 2 to about 150; and d is from 1 to about 6;

each $R^{12}$ is independently a bond, —$(C_{1-40})$alkylene- or branched —$(C_{1-40})$alkylene-groups, wherein each $R^{12}$ is optionally substituted with one or more (e.g., 1, 2, or 3) functional groups; and $X^4$ is —O—, —S—, or —N($R^7$)—;

wherein n is from 2 to 12; provided that a and b are not both zero; wherein each $R^7$ is independently selected from the group consisting of hydrogen, and $C_{(1-40)}$ alkyl group, where the alkyl group can be a straight-chain or branched group; and $R^a$ and $R^b$ are each independently hydrogen $(C_{1-8})$alkyl, aryl, aryl$(C_{1-8})$alkylene; and $R^6$ is hydrogen, —OH, —$OR^a$, —$NR^aR^b$, —$CO_2H$, —$SO_3H$ (sulfo), —$CH_2$—OH, —$CH_2$—$OR^a$, —$CH_2$—O—$CH_2$—$R^a$, —$CH_2$—$NR^aR^b$ or a targeting moiety; and e is from 1 to about 6.

4. The compound of claim 2, wherein $R^2$ has the formula:

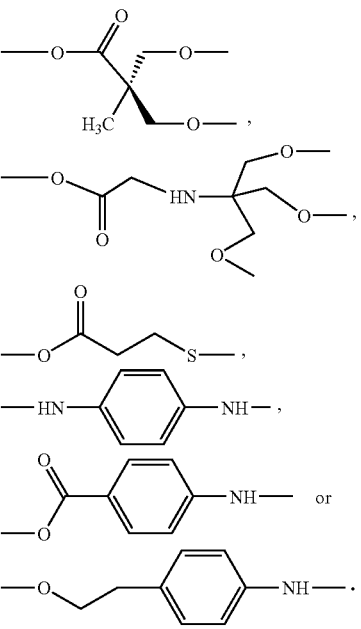

5. The compound of claim 2, wherein $R^2$ has the formula:

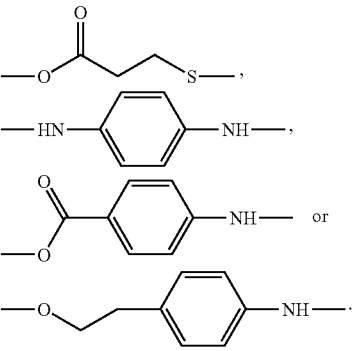

6. The compound of claim 2, wherein $R^2$ has the formula:

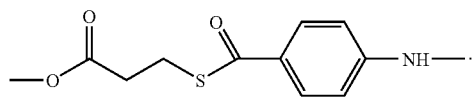

7. The compound of claim 2, wherein the $R^1$-$R^2$ combination has the formula:

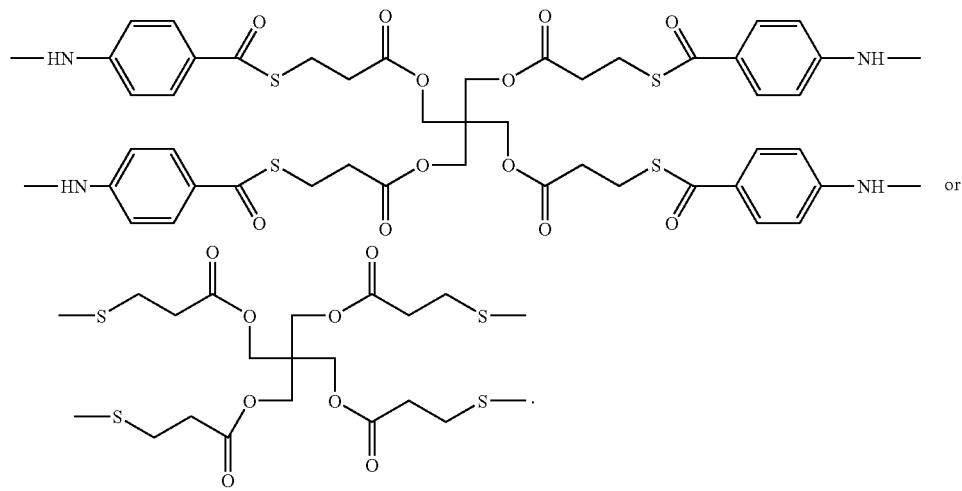

8. The compound of claim 1, wherein $R^3$ has the formula

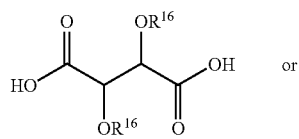

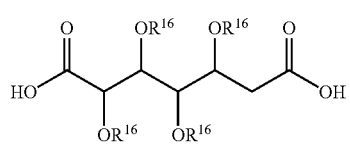

wherein each $R^{16}$ is an alkanoyl group having from 2 to about 24 carbon atoms.

9. The compound of claim 1, wherein $R^3$ is

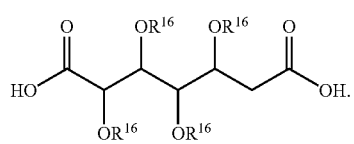

10. The compound of claim 8, wherein $R^{16}$ is an alkanoyl group having from about 6 to about 18 carbon atoms.

11. The compound of claim 1, wherein $R^1$ has from about 2 carbons to about 20 carbons.

12. The compound of claim 1, wherein $R^1$ has from about 3 carbons to about 12 carbons.

13. The compound of claim 1, wherein the $R^1$ moeity has from about 4 carbons to about 10 carbons.

14. The compound of claim 1, wherein $R^1$ is a cycloaliphatic polyol.

15. The compound of claim 1, wherein $R^1$ is a polyacid having the formula

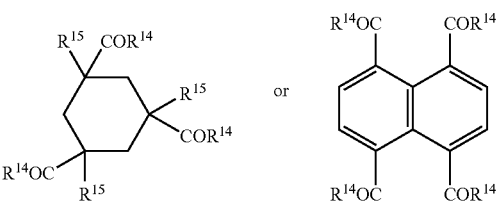

or a polyol having the formula

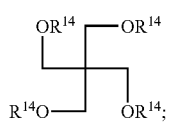

wherein each $R^{14}$ is $-(R^2)_a-(R^3)_b-(R^4)_c-(R^5)_d-(R^6)_e$; and wherein $R^{15}$ is hydrogen or $(C_{1-6})$alkyl.

16. The compound of claim 15, where $R^{15}$ is alkyl.

17. The compound of claim 16, where $R^{15}$ is methyl, ethyl, or propyl.

18. The compound of claim 17, where $R^{15}$ is methyl, or propyl.

19. The compound of claim 2, wherein $R^2$ is $-C(=O)-CH_2-CH_2-S-$.

20. The compound of claim 2, wherein the $R^1$-$R^2$ combination is pentaerythritol tetrakis(3-mercaptopropionate).

21. The compound of claim 1, wherein the $R^1$ moeity is substituted with one or more carboxy groups.

22. The compound of claim 1, wherein the $R^1$ moeity is substituted with two carboxy groups.

23. The compound of claim 1, wherein the $R^1$ moeity is substituted with one carboxy group.

24. The compound of claim 1, wherein $R^4$ has the formula:

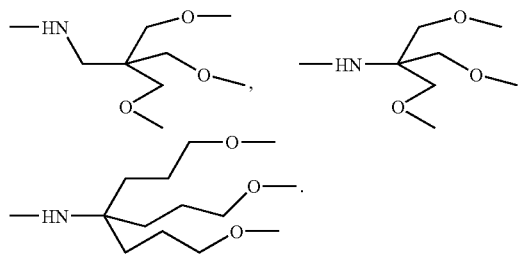

25. The compound of claim 1, wherein $R^5$ has the formula:

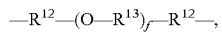

wherein $R^{13}$ is a 1 to 20 carbon straight-chain or branched alkyl group, wherein each $R^{12}$ is optionally substituted with one or more functional groups selected from the group consisting of —OH, —$OR^a$, —$NR^aR^b$, —$CO_2H$, —$SO_3H$, —$CH_2$—$OR^a$, —$CH_2$—O—$CH_2$—$R^a$, —$CH_2CO_2H$, —$CH_2SO_3H$, —O—C(=O)—$CH_2$—$CH_2$—C(=O)—O— or —$CH_2$—$NR^aR^b$;

Q is —O—, —S—, and —$NR^a$—; and $R^{12}$ is a 1 to 10 carbon straight-chain or branched divalent alkylene group;

$R^a$ and $R^b$ are each independently hydrogen $(C_{1-6})$alkyl, aryl, aryl$(C_{1-8})$alkylene f is an integer from 2 to 150, inclusive.

26. The compound of claim 1, wherein the $R^5$ is a polyethylene ether having between about 2 and about 110 alkylene oxide repeating units.

27. The compound of claim 26, wherein the alkylene oxide units containing from 2 to about 10 carbon atoms and may be straight chained or branched.

28. The compound of claim 26, wherein the alkylene oxide units contain from 2 to 4 carbon atoms and may be straight chained or branched.

29. The compound of claim 1 wherein $R^5$ is linked to $R^1$ through an ester, thioester, or amide linkage.

30. The compound of claim 1 wherein $R^5$ is linked to $R^1$ through an ester or amide linkage.

31. The compound of claim 1, wherein $R^5$ has the formula:

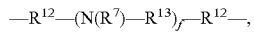

wherein each $R^{12}$ and $R^{13}$ are independently a 1 to 20 carbon straight-chain or branched alkyl group, wherein each $R^{12}$ is optionally substituted with one or more functional groups selected from the group consisting of —OH, —$OR^a$, —$NR^aR^b$, —$CO_2H$, —$SO_3H$, —$CH_2$—$OR^a$, —$CH_2$—O—$CH_2$—$R^a$, —$CH_2CO_2H$, —$CH_2SO_3H$, —O—C(=O)—$CH_2$—$CH_2$—C(=O)—O— or —$CH_2$—$NR^aR^b$;

Q is —O—, —S—, and —$NR^a$—; and $R^{12}$ is a 1 to 10 carbon straight-chain or branched divalent alkylene group;

$R^a$ and $R^b$ are each independently hydrogen $(C_{1-6})$alkyl, aryl, aryl$(C_{1-8})$alkylene f is an integer from 2 to 150, inclusive.

32. The compound of claim 1, wherein $R^5$ is a polyethylene imine having between about 2 and about 110 repeating units.

33. The compound of claim 32, wherein the polyethylene imine has units contain from 2 to about 10 carbon atoms.

34. The compound of claim 2, wherein $R^6$ is alkyl, aryl, biotin, streptavidin, a sugar moiety, folic acid, an amino acid or a peptide.

35. The compound of claim 1, wherein $R^6$ is the peptide Arg-Gly-Asp (R-G-D) or Tyr-Ile-Gly-Ser-Arg (Y—I-G-S—R).

36. The compound of claim 1, wherein $R^6$ is biotin.

37. The compound of claim 1, wherein the acid residue comprises from about 2 to about 24 carbon atoms.

38. The compound of claim 1, wherein the acid residue comprises from about 6 to about 18 carbon atoms.

39. The compound of claim 1 wherein the acid residue comprises caprylic, capric, lauric, myristic, myristoleic, palmitic, palmitoleic, stearic, oleic, linoleic, eleostearic, arachidic, behenic, erucic acid, or a mixture thereof.

40. The compound of claim 1, wherein the one or more functional groups are —OH, —ORa, —NRaRb, —CO2H, —SO3H (sulfo), —CH2—OH, —CH2—ORa, —CH2-O—CH2-Ra, or —CH2-NRaRb.

41. An encapsulate comprising a molecule surrounded or partially surrounded by at least one compound of formula (I), as described in claim 1.

42. An encapsulate comprising a therapeutic agent surrounded or partially surrounded by at least one compound of formula (I), as described in claim 1.

43. A composition comprising at least one compound of formula (I) as described in claim 1 in a solvent.

44. The composition of claim 43, wherein the solvent comprises an organic solvent.

45. The composition of claim 43, wherein the solvent comprises water.

46. The composition of claim 43, wherein the solvent is water.

47. A method for preparing an encapsulate as described in claim 42, comprising combining at least one compound of formula (I), as described in claim 1, and a molecule in a solvent; and allowing the compound of formula (I) to aggregate around the molecule, to provide the encapsulate.

48. A pharmaceutical composition comprising an encapsulate as described in claim 42; and a pharmaceutically acceptable carrier.

49. A method for delivering a therapeutic agent to an animal in need of treatment with the agent comprising administering an encapsulate as described in claim 42 to the animal.

50. The compound of claim 2, wherein $R^5$ has the formula:

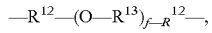

wherein $R^{13}$ is a 1 to 20 carbon straight-chain or branched alkyl group, wherein each $R^{12}$ is optionally substituted with one or more functional groups selected from the group consisting of —OH, —$OR^a$, —$NR^aR^b$, —$CO_2H$, —$SO_3H$, —$CH_2$—$OR^a$, —$CH_2$—O—$CH_2$—$R^a$, —$CH_2CO_2H$, —$CH_2SO_3H$, —O—C(=O)—$CH_2$—$CH_2$—C(=O)—O— or —$CH_2$—$NR^aR^b$;

Q is —O—, —S—, and —$NR^a$—; and $R^{12}$ is a 1 to 10 carbon straight-chain or branched divalent alkylene group;

$R^a$ and $R^b$ are each independently hydrogen $(C_{1-6})$alkyl, aryl, aryl$(C_{1-8})$alkylene f is an integer from 2 to 150, inclusive.

51. The compound of claim 2, wherein the $R^5$ is a polyethylene ether having between about 2 and about 110 alkylene oxide repeating units.

52. The compound of claim 2 wherein $R^5$ is linked to $R^1$ through an ester or amide linkage.

53. The compound of claim 2, wherein $R^5$ has the formula:

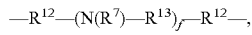

wherein each $R^{12}$ and $R^{13}$ are independently a 1 to 20 carbon straight-chain or branched alkyl group, wherein each $R^{12}$ is optionally substituted with one or more functional groups selected from the group consisting of —OH, —OR$^a$, —NR$^a$R$^b$, —CO$_2$H, —SO$_3$H, —CH$_2$—OR$^a$, —CH$_2$—O—CH$_2$—R$^a$, —CH$_2$CO$_2$H, —CH$_2$SO$_3$H, —O—C(=O)—CH$_2$—CH$_2$—C(=O)—O— or —CH$_2$—NR$^a$R$^b$;

Q is —O—, —S—, and —NR$^a$—; and $R^{12}$ is a 1 to 10 carbon straight-chain or branched divalent alkylene group;

$R^a$ and $R^b$ are each independently hydrogen $(C_{1-6})$alkyl, aryl, aryl$(C_{1-8})$alkylene f is an integer from 2 to 150, inclusive.

54. The compound of claim 2, wherein $R^5$ is a polyethylene imine having between about 2 and about 110 repeating units.

55. An encapsulate comprising a molecule surrounded or partially surrounded by at least one compound of formula (I), as described in claim 2.

56. A method for preparing an encapsulate as described in claim 55, comprising combining at least one compound of formula (I), as described in claim 2 and the molecule in a solvent; and allowing the compound of formula (I) to aggregate around the molecule, to provide the encapsulate.

57. A pharmaceutical composition comprising an encapsulate as described in claim 55 and a pharmaceutically acceptable carrier, wherein the molecule is a therapeutic agent.

58. A method for delivering a therapeutic agent to an animal in need of treatment with the therapeutic agent comprising administering a composition as described in claim 57 to the animal.

* * * * *